United States Patent
Dittamore

(10) Patent No.: US 10,527,624 B2
(45) Date of Patent: Jan. 7, 2020

(54) CIRCULATING TUMOR CELL DIAGNOSTICS FOR PROSTATE CANCER BIOMARKERS

(71) Applicant: EPIC SCIENCES, INC., San Diego, CA (US)

(72) Inventor: Ryan Dittamore, San Diego, CA (US)

(73) Assignee: Epic Sciences, Inc., San Diego, CA (US)

(*) Notice: Subject to any disclaimer, the term of this patent is extended or adjusted under 35 U.S.C. 154(b) by 0 days.

(21) Appl. No.: 14/605,772

(22) Filed: Jan. 26, 2015

(65) Prior Publication Data

US 2016/0033508 A1 Feb. 4, 2016

Related U.S. Application Data

(60) Provisional application No. 61/932,096, filed on Jan. 27, 2014.

(51) Int. Cl.
*G01N 33/574* (2006.01)
*G01N 21/64* (2006.01)
*G01N 33/53* (2006.01)

(52) U.S. Cl.
CPC ....... *G01N 33/57434* (2013.01); *G01N 33/53* (2013.01); *G01N 2021/6439* (2013.01); *G01N 2021/6441* (2013.01)

(58) Field of Classification Search
None
See application file for complete search history.

(56) References Cited

U.S. PATENT DOCUMENTS

| | | | |
|---|---|---|---|
| 6,197,523 B1 | 3/2001 | Rimm et al. | |
| 6,701,197 B2 | 3/2004 | Ben-Ezra et al. | |
| 6,960,449 B2 | 11/2005 | Wang et al. | |
| 7,277,569 B2 | 10/2007 | Bruce et al. | |
| 7,280,261 B2 | 10/2007 | Curry et al. | |
| 7,282,180 B2 | 10/2007 | Tibbe et al. | |
| 7,305,112 B2 | 12/2007 | Curry et al. | |
| 7,546,210 B2 | 6/2009 | Callahan et al. | |
| 7,724,937 B2 | 5/2010 | So et al. | |
| 7,943,397 B2 | 5/2011 | Tibbe et al. | |
| 8,088,715 B2 | 1/2012 | Bodmer et al. | |
| 2002/0160443 A1 | 10/2002 | Tsipouras et al. | |
| 2002/0187485 A1 | 12/2002 | Jakobsen et al. | |
| 2003/0108529 A1 | 6/2003 | Nackman et al. | |
| 2003/0109059 A1 | 6/2003 | Adrien et al. | |
| 2003/0129676 A1 | 7/2003 | Terstappen et al. | |
| 2004/0029213 A1 | 2/2004 | Callahan et al. | |
| 2005/0003464 A1 | 1/2005 | Tibbe et al. | |
| 2005/0181463 A1 | 1/2005 | Rao et al. | |
| 2006/0024756 A1 | 2/2006 | Tibbe et al. | |
| 2007/0212698 A1 | 9/2007 | Bendele et al. | |
| 2007/0212736 A1 | 9/2007 | Chen-Kiang et al. | |
| 2008/0009019 A1 | 1/2008 | Haizlip et al. | |
| 2008/0007672 A1 | 3/2008 | Hoon et al. | |
| 2008/0076727 A1 | 3/2008 | Hoon et al. | |
| 2008/0090239 A1 | 4/2008 | Shoemaker et al. | |
| 2008/0113358 A1 | 5/2008 | Kapur et al. | |
| 2009/0029378 A1 | 1/2009 | Connelly et al. | |
| 2009/0072171 A1 | 3/2009 | So et al. | |
| 2009/0081688 A1 | 3/2009 | Luo et al. | |
| 2009/0105963 A1 | 4/2009 | Laursen et al. | |
| 2009/0317836 A1 | 12/2009 | Kuhn et al. | |
| 2010/0028915 A1 | 2/2010 | Gualberto et al. | |
| 2010/0048709 A1 | 2/2010 | Wafa et al. | |
| 2010/0184093 A1 | 7/2010 | Donovan et al. | |
| 2010/0184629 A1 | 7/2010 | Giffin et al. | |

(Continued)

FOREIGN PATENT DOCUMENTS

CN 1596265 A 3/2005
CN 101099104 A 1/2008

(Continued)

OTHER PUBLICATIONS

Mikolajczyk et al. "Detection of EpCAM-Negative and Cytokeratin-Negative Circulating Tumor Cells in Peripheral Blood" Journal of Oncology vol. 2011, Article ID 252361, 10 pages.*

Park et al. "Highly Efficient Assay of Circulating Tumor Cells by Selective Sedimentation with a Density Gradient Medium and Microfiltration from Whole Blood" Anal. Chem. 2012, 84, 7400-7407.*

StemCell Technologies "Frequencies of Cell Types in Human Peripheral Blood" available on Jun. 8, 2012 via Wayback Machine, 1pg.*

Chan et al., "Dramatically elevated circulating tumor cell numbers in a patient with small cell neuroendocrine carcinoma of the prostate," Arch. Pathol. Lab. Med., 134(1):120-123 (2010).

Park et al., "Morphological differences between circulating tumor cells from prostate cancer patients and cultured prostate cancer cells," PLoS One, 9(1):e85264 (2014).

(Continued)

*Primary Examiner* — Thane Underdahl
(74) *Attorney, Agent, or Firm* — Jones Day

(57) ABSTRACT

The present invention describes a method for detecting castration-resistant prostate cancer (CRPC) in a patient afflicted with prostate cancer comprising (a) performing a direct analysis comprising immunofluorescent staining and morphological characterization of nucleated cells in a blood sample obtained from the patient to detect circulating tumor cells (CTC), (b) determining prevalence of a CTC subpopulation associated with CRPC comprising detecting a measurable feature of each biomarker in a panel of morphological and protein biomarkers, and (c) comparing the prevalence of said CTC subpopulation to a predetermined threshold value, wherein the prevalence of the CTC subpopulation associated with CRPC above said predetermined threshold value is indicative of CRPC. In some embodiments, the CTC subpopulation associated with CRPC comprises CK– CTCs. In some embodiments, the CTC subpopulation associated with CRPC comprises small CTCs. In additional embodiments, the methods of the invention further comprise molecular analysis of the CTCs.

14 Claims, 16 Drawing Sheets

(56) References Cited

U.S. PATENT DOCUMENTS

| | | |
|---|---|---|
| 2010/0297634 A1 | 11/2010 | Chen |
| 2010/0300216 A1 | 12/2010 | Angros |
| 2011/0189670 A1 | 8/2011 | Katz et al. |
| 2011/0238325 A1 | 9/2011 | Lett et al. |
| 2011/0300551 A1 | 12/2011 | Rao et al. |
| 2012/0208706 A1 | 8/2012 | Lipson et al. |
| 2012/0276555 A1* | 11/2012 | Kuhn ............. G01N 33/5076 435/7.23 |
| 2013/0130241 A1 | 5/2013 | Dehm |
| 2013/0157347 A1 | 6/2013 | Topol et al. |
| 2013/0171642 A1 | 7/2013 | Pestano et al. |
| 2013/0252259 A1 | 9/2013 | Kuhn et al. |
| 2014/0024024 A1 | 1/2014 | Sood et al. |
| 2014/0031250 A1 | 1/2014 | Ting et al. |
| 2014/0308669 A1 | 10/2014 | Yang et al. |
| 2014/0329917 A1 | 11/2014 | Marienfeld et al. |
| 2015/0147339 A1 | 5/2015 | Olson et al. |
| 2015/0185204 A1 | 7/2015 | Kuhn et al. |
| 2015/0212089 A1 | 7/2015 | Dittamore |
| 2015/0233927 A1 | 8/2015 | Giannakakou et al. |
| 2016/0033508 A1 | 2/2016 | Dittamore |
| 2016/0040245 A1 | 2/2016 | Dittamore |
| 2016/0266127 A1 | 9/2016 | Kuhn et al. |
| 2016/0341732 A1 | 11/2016 | Dittamore |
| 2017/0010268 A1 | 1/2017 | Marrinucci |
| 2017/0192003 A1 | 7/2017 | Kuhn et al. |
| 2017/0242016 A1 | 8/2017 | Dittamore |
| 2017/0285035 A1 | 10/2017 | Dittamore |
| 2018/0052167 A1 | 2/2018 | Dittamore |
| 2018/0100857 A1 | 4/2018 | Kuhn et al. |
| 2018/0155794 A1 | 6/2018 | Dittamore et al. |
| 2018/0321247 A1 | 11/2018 | Dittamore et al. |
| 2019/0025312 A1 | 1/2019 | Dittamore et al. |

FOREIGN PATENT DOCUMENTS

| | | |
|---|---|---|
| CN | 101511481 A | 8/2009 |
| CN | 101226118 B | 6/2010 |
| DE | 3830721 A1 | 3/1990 |
| EP | 0919812 A2 | 6/1999 |
| WO | WO 1999/41613 A1 | 8/1999 |
| WO | WO 2006/041453 A1 | 4/2006 |
| WO | WO 2007/089911 A2 | 8/2007 |
| WO | WO 2008/030381 A2 | 3/2008 |
| WO | WO 2009/051734 | 4/2009 |
| WO | 2009/120767 A1 | 10/2009 |
| WO | WO 2011/050103 A1 | 4/2011 |
| WO | WO 2011/093927 A1 | 8/2011 |
| WO | 2012/103025 A2 | 8/2012 |
| WO | WO 2013/049926 A1 | 4/2013 |
| WO | 2013/086428 A1 | 6/2013 |
| WO | 2013/111054 A1 | 8/2013 |
| WO | 2013/181532 A1 | 12/2013 |
| WO | 2014/008155 A1 | 1/2014 |
| WO | WO 2014/008155 * | 1/2014 |
| WO | WO 2014/066864 A2 | 5/2014 |
| WO | WO 2014/120265 A1 | 8/2014 |
| WO | WO 2014/151006 A2 | 9/2014 |
| WO | WO 2015/048740 A1 | 4/2015 |
| WO | WO 2015/112955 A1 | 7/2015 |
| WO | WO 2015/112999 A1 | 7/2015 |
| WO | WO 2015/116828 A1 | 8/2015 |

OTHER PUBLICATIONS

Cho et al., "Characterization of circulating tumor cell aggregates identified in patients with epithelial tumors," Phys. Biol., 9:016001 (2012).
Kang et al., "A combined micromagnetic-microfluidic device for rapid capture and culture of rare circulating tumor cells," Lab. Chip.,12:2175-2181 (2012).
Park et al., "Highly efficient assay of circulating tumor cells by selective sedimentation with a density gradient medium and microfiltration from whole blood," Anal. Chem., 84:7400-7407 (2012).
Pierga et al., "High independent prognostic and predictive value of circulating tumor cells compared with serum tumor markers in a large prospective trial in first-line chemotherapy for metastatic breast cancer patients," Annals. Oncol., 23:618-624 (2012).
Punnoose et al., "Evaluation of circulating tumor cells and circulating tumor DNA in non-small cell lung cancer: association with clinical endpoints in a phase II clinical trial of pertuzumab and erlotinib," Clin. Cancer Res., 18(8):1-11 (2012).
Aberle et al., "Reduced lung-cancer mortality with low-dose computed tomographic screening," N. Engl. J. Med., 365(5):395-409 (2011).
Aggarwal et al., "Neuroendocrine prostate cancer: subtypes, biology, and clinical outcomes," J. Natl. Compr. Canc. Netw., 12(5):719-726 (2014).
Alix-Panabières et al., "Circulating tumor cells and circulating tumor DNA," Annu. Rev. Med., 63:199-215 (2012).
Alix-Panabières et al., "Circulating tumor cells: liquid biopsy of cancer," Clin. Chem., 59(1):110-118 (2013).
Allard et al., "Tumor cells circulate in the peripheral blood of all major carcinomas but not in healthy subjects or patients with nonmalignant diseases," Clin. Cancer Res., 10(20):6897-6904 (2004).
Amato et al., "Epithelial cell adhesion molecule-positive circulating tumor cells as predictive biomarker in patients with prostate cancer," Urology, 81(6):1303-1307 (2013).
Angerer et al., "Demonstration of tissue-specific gene expression by in situ hybridization," Methods Enzymol., 152:649-661 (1987).
Antonarakis et al., "AR-V7 and resistance to enzalutamide and abiraterone in prostate cancer," N. Engl. J. Med., 371(11):1028-1038 (2014).
Aparico et al., "Platinum-based chemotherapy for variant castrate-resistant prostate cancer," Clin. Cancer Res., 19(13):3621-3630 (2013).
Armstrong et al., "Biomarkers in the management and treatment of men with metastatic castration-resistant prostate cancer," Eur. Urol., 61(3):549-559 (2012).
Arya et al., "Enrichment, detection and clinical significance of circulating tumor cells," Lab. Chip., 13(11):1995-2027 (2013).
Asworth, "A case of cancer in which cells similar to those in the tumours were seen in the blood after death," Australian Med. J., 14: 146-147 (1869).
Attard et al., "Characterization of ERG, AR and PTEN gene status in circulating tumor cells from patients with castration-resistant prostate cancer," Cancer Res., 69(7):2912-2918 (2009).
Autio et al., "Heterogeneity of prostate-specific membrane antigen expression in traditional and apoptotic circulating tumor cells in metastatic castration-resistant prostate cancer," American Society of Clinical Oncology Genitourinary (ASCO GU) conference, Jan. 30, 2014, San Francisco, CA, Abstract 198.
Balic et al., "Circulating tumor cells: from bench to bedside," Annu. Rev. Med., 63:31-44 (2013).
Balic et al., "Progress in circulating tumor cell capture and analysis: implications for cancer management," Expert Rev. Mol. Diagn., 12(3):303-312 (2012).
Beltran et al., "Aggressive variants of castration-resistant prostate cancer," Clin. Cancer Res., 20(11):2846-2850 (2014).
Beltran et al., "Challenges in recognizing treatment-related neuroendocrine prostate cancer," J. Clin. Oncl., 30(36):e386-e389 (2012).
Beltran et al., "Molecular characterization of circulating tumor cells of patients with neuroendocrine prostate cancer," American Society of Clinical Oncology Genitourinary (ASCO GU) conference, Jan. 30, 2014, San Francisco, CA, Abstract 177.
Beltran et al., "Molecular characterization of neuroendocrine prostate cancer and identification of new drug targets," Cancer Discov., 1(6):487-495 (2011).
Beltran et al., "New strategies in prostate cancer: translating genomics into the clinic," Clin. Cancer Res., 19(3):517-523 (2013).
Bovee et al., "Loss of heterozygosity and DNA ploidy point to a diverging genetic mechanism in the origin of peripheral and central chondrosarcoma," Genes, Chromosomes & Cancer, 26:237-246 (1999).

(56) References Cited

OTHER PUBLICATIONS

Box et al., "An analysis of transformations," *J. Royal Statist. Soc.*, Series B, 26(2):211-243 (1964).
Brandt et al., "Isolation of prostate-derived single cells and cell clusters from human peripheral blood," *Cancer Res.*, 56(20):4556-4561 (1996).
Breiman, "Random Forests," *Machine Learning*, 45:5-32 (2001).
Brenner et al., "ETS Fusion Genes in Prostate Cancer," *Prostate Cancer: Biochemistry, Molecular Biology and Genetics*, Tindall ed., Springer, New York, 16:139-183 (2013).
Chang et al., "High-risk prostate cancer-classification and therapy," *Nat. Rev. Clin. Oncol.*, 11(6):308-323 (2014).
Chinen et al., "Cytokeratin-based CTC counting unrelated to clinical follow up," *J. Thorac. Dis.*, 5(5):593-599 (2013).
Cohen et al., "Prognostic significance of circulating tumor cells in patients with metastatic colorectal cancer," *Ann. Oncol.*, 20(7):1223-1229 (2009).
Cohen et al., "Relationship of circulating tumor cells to tumor response, progression-free survival, and overall survival in patients with metastatic colorectal cancer," *J. Clin. Oncol.*, 26(19):3213-3221 (2008).
Cookson et al., "Castration-resistant prostate cancer: AUA Guideline," *J. Urol.*, 190(2):429-438 (2013).
Cristofanilli et al., "Circulating tumor cells, disease progression, and survival in metastic breast cancer," *N. Engl. J. Med.*, 351(8):781-791 (2004).
Cristofanilli et al., "Circulating tumor cells: a novel prognostic factor for newly diagnosed metastatic breast cancer," *J. Clin. Oncol.*, 23(7): 1420-1430 (2005).
Cristofanilli, "The biological information obtainable from circulating tumor cells," *Breast*, 3:S38-S40 (2009).
Curry et al., "High-speed detection of occult tumor cells in peripheral blood," Proceedings at the 26$^{th}$ Annual International Conference of *IEEE EMBS*, San Francisco, CA, Sep. 1-5, 1267-1270 (2004).
Danila et al., "Circulating tumor cell No. And prognosis in progressive castration-resistant prostate cancer," *Clin. Cancer Res.*, 13(23):7053-7058 (2007).
Danila et al., "Circulating tumors cells as biomarkers: progress toward biomarker qualification," *Cancer J.*, 17(6):438-450 (2011).
De Bono et al., "Circutlating tumor cells predict survival benefit from treatmetn in metastatic castration-resistant prostate cancer," *Clin. Cancer Res.*,14(19):6302-6309 (2008).
Diamond et al., "Isolation and characterization of circulating tumor cells in prostate cancer," *Front Oncol.*, 2:131 (2012).
Dittamore et al., "Molecuar characterization of circulating tumor cells (CTCs) and CTC subpopulations in progressive metastatic castration-restitant prostate cancer (mCRPC)," American Society of Clinical Oncology Genitourinary (ASCO GU) conference, Jan. 30, 2014, San Francisco, CA, Abstract 132.
European Patent Office, Extended European Search Report for EP Application No. 10825626.4, dated Apr. 18, 2013.
Fehm et al., "Methods for isolating circulating epithelial cells and criteria for their classification as carcinoma cells," *Cytotherapy*, 7(2):171-185 (2005).
Ferraldeschi et al., "CK- and small nuclear size circulating tumor cell phenotypes in metastatic castration-resistant prostate cancer," American Society of Clinical Oncology Genitourinary (ASCO GU) conference, Jan. 30, 2014, San Francisco, CA, Abstract 209.
Gazzaniga et al., "Circulating tumor cells: highlight on practical implications," *Mol. Diagn. Ther.*, 16(1):7-11 (2012).
Giordano et al., "Epithelial-mesenchymal transition and stem cell markers in patients with HER2-positive metastatic breast cancer," *Mol. Cancer Ther.*, 11(11):2526-2534 (2012).
Gorges et al., "Circulating tumor cells as therapy-related biomarkers in cancer patients," *Cancer Immunol. Immunother.*,62(5):931-939 (2013).
Gorges et al., "Circulating tumour cells escape from EpCAM-based detection due to epithelial-to-mesenchymal transition," *BMC Cancer*, 12:178 (2012).
Grasso et al., "The mutational landscape of lethal castration-resistant prostate cancer," *Nature*, 287(7406):239-243 (2012).
Hager et al., "The use of a panel of monoclonal antibodies to enrich circulating breast cancer cells facilitates their detection," *Gynecol. Oncol.*, 98(2):211-216 (2005).
Hanash et al., "Mining the plasma proteome for cancer biomarkers," *Nature*, 452(7187):571-579 (2008).
Hofman et al., "Preoperative circulating tumor cell detection using the isolation by size of epithelial tumor cell method for patients with lung cancer is a new prognostic biomarker," 17(4):827-835 (2011).
Hsieh et al., "High speed detection of circulating tumor cells," *Biosen. Bioelectron.*, 21(10):1893-1899 (2006).
Ignatiadis et al., "Prognostic value of the molecular detection of circulating tumor cells using a multimarker reverse transcription-PCR assay for cytokeratin 19, mammaglobin A, and HER2 in early breast cancer," *Clin. Cancer Res.*, 14(9):2593-2600 (2008).
Ihaka et al., "A langauge for data analysis and graphics," *J. Comput. Graph. Statist.*, 5(3):299-314 (2012).
Ioannidis, "Why most published research findings are false," *PLoS Med.*, 2(8):e124 (2005).
Jones et al., "Wright-Giemsa cytology of body fluids," *Laboratory Medicine*, 28(11):713-716 (1997).
Joosse et al., "Biologic challenges in the detection of circulating tumor cells," *Cancer Res.*, 73(1):8-11 (2013).
Kalluri et al., "The basics of epithelial-mesenchymal transition," *J. Clin. Invest.*, 119(6):1420-1428 (2009).
Kolatkar et al., "C-ME: a 3D community-based, real-time collaboration tool for scientific research and training," *PLoS One*, 3(2):e1621 (2008).
Kraeft et al., "Detection and analysis of lung cancer cells from body fluids using a rare event imaging system," *Methods Mol. Med.*, 75:423-430 (2003).
Kraeft et al., "Detection and anlysis of cancer cells in blood and bone marrow using a rare event imaging system," *Clin. Cancer Res.*, 6:434-442 (2000).
Kraeft et al., "Reliable and sensitive identificaiton of occult tumor cells using the improved rare event imaging system," *Clin. Cancer Res.*, 10(9):3020-3028 (2004).
Krebs et al., "Molecular analysis of circulating tumour cells-biology and biomarkers," *Nat. Rev. Clin. Oncol.*, 11(3):129-144 (2014).
Krebs et al., "Evaluation and prognostic significance of circulating tumor cells in patients with non-small-cell lung cancer," *J. Clin. Oncol.*, 29(12): 1556-1563 (2011).
Krivacic et al., "A rare-cell detector for cancer," *PNAS USA*, 101(29):10501-10504 (2004).
Kuhn et al., "A fluid biopsy as investigating technology for the fluid phase of solid tumors," *Phys. Biol.*, 9(1): 010301 (2012).
Ligthart et al., "Unbiased and automated identification of a circulating tumour cell definition that associates with overall survival," *PLoS One*, 6(11):e27419 (2011).
Lin et al., "Portable filter-based microdevice for detection and characterization of circulating tumor cells," *Clin. Cancer Res.*, 16(20):5011-5018 (2010).
Liotta et al., "The significance of hematogenous tumor cell clumps in the metastatic process," *Cancer Res.*, 36(3):889-894 (1976).
Lucci et al., "Circulating tumour cells in non-metastatic breast cancer: a prospective study," *Lancet Oncol.*, 13(7):688-695 (2012).
Maheswaran et al., "Detection of mutations in EGFR in circulating lung-cancer cells," *N. Eng. J. Med.*, 359(4):366-377 (2008).
Marrinucci et al., "Circulating tumor cells from well-differentiated lung adenocarcinoma retain cytomorphologic features of primary tumor type," *Arch. Pathol. Lab. Med.*, 133(9):1468-1471 (2009).
Marrinucci et al., "Cytomorphology of circulating colorectal tumor cells:a small case series," *J. Oncol.*, 2010:861341 (2010).
Marrinucci et al., "Case study of the morphologic variation of circulating tumor cells," *Hum. Pathol.*, 38(3):514-519 (2007).
Marrinucci et al., "Fluid biopsy in patients with metastatic prostate, pancreatic and breast cancers," *Phys. Biol.*, 9(1):016003 (2012).
Mateo et al., "The promise of circulating tumor cell analysis in cancer management," *Genome Biol.*, 15(8):448 (2014).
Meng et al., "Circulating tumor cells in patients with breast cancer dormancy," *Clin. Cancer Res.*, 10(24):8152-8162 (2004).

(56) References Cited

OTHER PUBLICATIONS

Mezynski et al., "Antitumour activity of docetaxel following treatment with the CYP17A1 inhibitor abiraterone: clinical evidence for cross-resistance?," *Ann. Oncol.*, 23(11):2943-2947 (2012).
Miller et al., "Significance of circulating tumor cells detected by the CellSearch System in patients with metastatic breast colorectal and prostate cancer," *J. Oncol.*, 2010:617421 (2010).
Miyake et al., "Alpha-fetoprotein and human chorionic gonadotropin- producing lung cancer," *Cancer*, 59(2):227-232 (1987).
Miyamoto et al., "Androgen receptor signaling in circulating tumor cells as a marker of hormonally responsive prostate cancer," *Cancer Discov.*, 2(11):995-1003 (2012).
Mohler et al., "Prostate cancer, version 1.2014," *J. Natl. Compr. Canc. Netw.*, 11(12):1471-1479 (2013).
Mohler et al., "Prostate cancer, version 2.2014," *J. Natl. Compr. Canc. Netw.*, 12(5):686-718 (2014).
Molnar et al., "Circulating tumor cells clusters in the peripheral blood of colorectal cancer patients," *Clin. Cancer Res.*, 7(12):4080-4085 (2001).
Mosquera et al., "Concurrent AURKA and MYCN gene amplifications are harbingers of lethal treatment-related neuroendocrine prostate cancer," *Neoplasia*, 15(1):1-10 (2013).
Nagrath et al., "Isolation of rare circulating tumour cells in cancer patients by microchip technology," *Nature*, 450(7173):1235-1239 (2007).
Nair et al., "An observational study of circulating tumor cells and $^{18}$F-FDG PET uptake in patients with treatment-naive non-small cell lung cancer," *PLoS One*, 8(7):e67733 (2013).
Nair et al., "Clinical outcome prediction by microRNAs in human cancer: a systematic review," *J. Natl. Cancer Inst.*, 104(7): 528-540 (2012).
Nieva et al., "High-definition imaging of circulating tumor cells and associated cellular events in non-small cell lung cancer patients: a longitudinal analysis," *Phys. Biol.*, 9(1):016004 (2012).
Noonan et al., "Clinical activity of abiraterone acetate in patients with metastatic castration-resistant prostate cancer progressing after enzalutamide," Ann. Oncol., JD 24(7):1802-1807 (2013).
Olmos et al., "Circulating tumour cell (CTC) counts as intermediate end points in castration-resistant prostate cancer (CRPC): a single-centre experience," *Ann. Oncol.*, 20(1):27-33 (2009).
Ozkumur et al., "Inertial focusing for tumor antigen-dependent and -independent sorting of rare circulating tumor cells," *Sci. Transl. Med.*, 5(179):179ra47 (2013).
Pantel et al., "The potential of circulating tumor cells as a liquid biopsy to guide therapy in prostate cancer," *Cancer Discov.*,2(11):974-975 (2012).
Pantel et al., "Circulating epithelial cells in patients with benign colon diseases," *Clin. Chem.*, 58(5):936-940 (2012).
Parkinson et al., "Considerations in the development of circulating tumor cell technology for clinical use," *J. Transl., Med.*, 10:138 (2012).
Pecot et al., "A novel platform for detection of CK+ and CK− CTCs," *Cancer Discov.*, 1(7):580-586 (2011).
Pezaro et al., "Activity of cabazitaxel in castration-resistant prostate cancer progressing after docetaxel and next-generation endocrine agents," *Eur. Urol.*, 66(3):459-465 (2014).
Picard et al., "Cross-validation of regression models," *J. Am. Statist. Assoc.*, 79(387):575-583 (1984).
Polzer et al., "Molecular profiling of single circulating tumor cells with diagnostic intention," *EMBO Mol. Med.*, 6(11):1371-1386 (2014).
Qimaging, "Retiga EXi Fast 1394 User's Manual," Quantitative Imaging Corporation, (2003).
Rami-Porta et al., "The IASLC Lung Cancer Staging Project: proposals for the revision of the T descriptors in the forthcoming (seventh) edition of the TNM classification for lung cancer," *J. Thorac. Oncol.*, 2(7):593-602 (2007).
Reyal et al., "Circulating tumor cell detection and transcriptomic profiles in early breast cancer patients," *Ann. Oncol.*, 22(6):1458-1459 (2011).
Reyes et al., "Quantitative characterization of androgen receptor protein expression and cellular localization in circulating tumor cells from patients with metastatic castration-resistant prostate cancer," *J. Transl. Med.*, 12(1):313 (2014).
Romsdahl et al., "The time of metastasis and release of circulating tumor cells as determined in an experimental system," *Cancer*, 14:883-888 (1961).
Roudier et al., "Phenotypic heterogeneity of end-stage prostate carcinoma metastatic to bone," *Hum. Pathol.*, 34(7):646-653 (2003).
Santoni et al., "Neuroendocrine differentiation in prostate cancer: novel morphological insights and future therapeutic perspectives," *Biochim. Biophys. Acta.*, 1846(2):630-637 (2014).
Scheel et al., "Cancer stem cells and epithelial-mesenchymal transition: concepts and molecular links," *Semin. Cancer Biol.*, 22(5-6):396-403 (2012).
Scher et al., "Circulating tumour cells as prognostic markers in progressive, castration-resistant prostate cancer: a reanalysis of IMMC38 trial data," *Lancet Oncol.*, 10(3):233-239 (2009).
Schreuder, "Laser Image Cytometer for Analysis of Circulating Tumor Cells," Wöhrmann Print Sevice, Zutphen, The Netherlands, 166 pages (2008).
Schultz et al., "Validation of two models to estimate the probability of malignancy in patients with solitary pulmonary nodules," *Thorax*, 63(4):335-341 (2008).
Scotton et al., "Epithelial cancer cell migration: a role for chemokine receptors?," *Cancer Res.*, 61(13):4961-4965 (2001).
Self et al., "Advances in immunoassay technology," *Curr. Opin. Biotchnol.*, 7(1):60-65 (1996).
Shah et al., "Androgen-independent prostate cancer is a heterogeneous group of diseases: lessons from a rapid autopsy program," *Cancer Res.*, 64(24):9209-9216 (2004).
Shankar et al., "Consensus recommendations for the use of $^{18}$F-FDG PET as an indicator of therapeutic response in patients in National Cancer Institute Trials," *J. Nucl. Med.*, 47(6):1059-1066 (2006).
Siegel et al., "Cancer statistics, 2014," *CA Cancer J. Clin.*,64(1):9-29 (2014).
Somlo et al., "Multiple biomarker expression on circulating tumor cells in comparison to tumor tissues from primary and metastatic sites in patients with locally advanced/inflammatory, and stage IV breast cancer, using a novel detection techonlogy," *Breast Cancer Res. Treat.*, 128(1):155-163 (2011).
Stott et al., "Isolation and characterization of circulating tumor cells from patients with localized and metastic prostate cancer," *Sci. Transl. Med.*, 2(25):25ra23 (2010).
Tagawa, "Neuroendocrine prostate cancer after hormonal therapy: knowing is half the battle," *J. Clin. Oncol.*, 32(30):3360-3364 (2014).
Takahashi, "An experimental study of metastasis," *J. Path. Bacter.*, 20(1): 1-13 (1915).
Tanaka et al., "Circulating tumor cell as a diagnostic marker in primary lung cancer," *Clin. Cancer Res.*, 15(22):6980-6986 (2009).
Tanaka et al., "Circulating tumor cells (CTCs) in lung cancer: current status and future perspectives," *Lung Cancer: Targets and Therapy*, 1:77-84 (2010).
Tibshirani, "Regression skrinkage and selection via the lasso," *J. Royal Statist Soc.*, Series B, 58(1):267-288 (1996).
Vincent et al., "Carcinoembryonic antigen in 228 patients with carcinoma of the lung," *Cancer*, 36(6):2069-2076 (1975).
Vona et al., "Isolation by size of epithelial tumor cells : a new method for the immunomorphological and molecular characterization of circulatingtumor cells," *Am. J. Pathol.*, 156(1):57-63 (2000).
Watanabe et al., "Multicolor detection of rare tumor cells in blood using a novel flow cytometry-based system," *Cytometry A.*, 85(3):206-213 (2014).
Waters, "Accuracy and precision in quantitative fluorescence microscopy," *J. Cell Biol.*, 185(7):1135-1148 (2009).
Wendel et al., "Fluid biopsy for circulating tumor cell identification in patients with early-and late-stage non-small cell lung cancer: a glimpse into lung cancer biology," *Phys. Biol.*, 9(1):016005 (2012).

(56) References Cited

OTHER PUBLICATIONS

Witzig et al., "Detection of circulating cytokeratin-positive cells in the blood of breast cancer patients using immunomagnetic enrichment and digital microscopy," Clin. Cancer Res., 8(5):1085-1091 (2002).
Yap et al., "Circulating tumor cells: a multifunctional biomarker," Clin. Cancer Res., 20(10):2553-2568 (2014).
Yu et al., "Circulating breast tumor cells exhibit dynamic changes in epithelial and mesenchymal composition," Science, 339(6119):580-584 (2013).
Zhang et al., "The identification and characterization of breast cancer CTCs competent for brain metastasis," Sci. Transl. Med., 5(180):180ra48 (2013).
Zlotta et al., "Prevalence of prostate cancer on autopsy: cross-sectional study on unscreened Caucasian and Asian men," J. Natl. Cancer Inst., 105(14):1050-1058 (2013).
Leversha et al., "Fluorescence in situ hybridization analysis of circulating tumor cells in metastatic prostate cancer," Clin. Cancer Res., 15:2091-2097 (2009).
Nagle et al., "ERG overexpression and PTEN status predict capsular penetration in prostate carcinoma," Prostate, 73(11):1233-1240 (2013).
Rickman et al., "ERG cooperates with androgen receptor in regulating trefoil factor 3 in prostate cancer disease progression," Neoplasia,12(12):1031-1040 (2010).
Zhang et al., "Androgen receptor variants occur frequently in castration resitant prostate cancer metastases," PLoS One, 6(11):e27970 (2011).
Hou et al., "Isolation and retrieval of cirulating tumor cells using centrifugal forces," Scientific Reports, 3(1259):1-8 (2013).
Jung et al., "Fluorescence quenching of green fluorescent protein during denaturation by guanidine," Bull.Korean Chem. Soc., 26(3):413-417 (2005).
Stepanenko et al., "Distinct effects of guanidine thiocyanate on the structure of superfolder GFP," PLoS One, 7(11):e48809 (2012).
Abkevich et al., "Patterns of genomic loss of heterozygosity predict homologous recombination repair defects in epithelial ovarian cancer," Br. J. Cancer, 107(10):1776-1782 (2012).
Anonymous, "Circulating tumor cell," Wikipepia, Jan. 13, 2015, retrieved from the internet: URL:https://en.wikipedia.org/w/index.php?title=Circulating_tumor_cell&oldid=642235295 [retrieved on May 3, 2018], 14 pages.
Antonarakis et al., "Androgen Receptor Splice Variant 7 and Efficacy of Taxane Chemotherapy in Patients With Metastatic Castration-Resistant Prostate Cancer," JAMA Oncol., 1(5):582-591 (2015).
Antonarakis et al., "AR splice variant (AR-V7) and response to taxanes in men with metastatic castration-resistant prostate cancer (mCRPC)," J. Clin. Oncol., 33(7):138 (2015).
*Ariosa Diagnostics Center, Inc.* v. *Sequenom, Inc.*, Opinion of the United States Court of Appeals for the Federal Circuit, pp. 1-21 (2015).
Armstrong et al., "Circulating tumor cells from patients with advanced prostate and breast cancer display both epithelial and mesenchymal markers," Mol. Cancer Res., 9(8):997-1007 (2011).
Arora et al., "Glucocorticoid receptor confers resistance to antiandrogens by bypassing androgen receptor blockade," Cell, 155(6):1309-1322 (2013).
Attard et al, "Utilizing circulating tumor cells: challenges and pitfalls," Curr. Opin. Gen. Dev., 21:50-58 (2011).
Attard et al., "Selective inhibition of CYP17 with abiraterone acetate is highly active in the treatment of castration-resistant prostate cancer," J. Clin. Oncol., 27(23):3742-3748 (2009).
Balmana et al., "Phase I trial of olaparib in combination with cisplatin for the treatment of patients with advanced breast, ovarian and other solid tumors," Ann. Oncol., 25(8):1656-1663 (2014).
Bambury et al., "Characteristics of de novo reistance to androgen targeting therapeutics (AR TX) through circulating tumor cells (CTCS) analysis in metastatic castration resistant prostate cancer (MCRPC) patients," Annals. Oncol., 25(Suppl. 4):iv58-iv84, Abstract 237P (2014).

Becker et al., "New frontiers in circulating tumor cell analysis: A reference guide for biomolecular profiling toward translational clinical use," Int. J. Cancer, 134(11):2523-2533 (2014).
Beltran et al., "The initial detection and partial characterization of circulating tumor cells in neuroendocrine prostate cancer," Clin. Cancer Res., 22(6):1510-1519 (2016).
Borgen et al., "Use of automated microscopy for the deteection of disseminated tumor cells in bone marrow samples," Cytometry, 46:215-221 (2001).
Brenner et al., "Gene expression analysis by massively parallel signature sequencing (MPSS) on microbead arrays," Nat. Biotechnol., 18(6):630-634 (2000).
Chang, "Treatment options for hormone-refractory prostate cancer," Rev. Urol., 9(Suppl 2):S13-S18 (2007).
Chen et al., "Clinical significance of programmed death-1 ligand-1 expression in patients with non-small cell lung cancer: a 5-year-follow-up study," Tumori, 98(6):751-755 (2012) Abstract only.
Cloonan et al., "Stem cell transcriptome profiling via massive-scale mRNA sequencing," Nat. Methods,5(7):613-619 (2008).
Darshan et al., "Taxane-induced blockade to nuclear accumulation of the androgen receptor predicts clinical responses in metastatic prostate cancer," Cancer Res., 71(18):6019-6029 (2011).
Del Conte et al., "Phase I study of olaparib in combination with liposomal doxorubicin in patients with advanced solid tumours," Br. J. Cancer, 111(4):651-659 (2014).
Etzioni et al., "The case for early detection," Nature Rev., 3:1-10 (2003).
Friedlander et al., "Detection and genomic interrogation of circulating tumor cells (CTCs) and circulating tumor stem cells (CTSCs) from men with metastatic castration-resistant prostate cancer (mCRPC)," Eur. J. Cancer, 48(Supp 6):152, Abstract 490 (2012).
Gibbs et al., "Abstract 4816: Development of an integrated analysis platform of circulating melanoma cells for PD-L1 expression as a predictive biomarker," Cancer Res., 74(19 Suppl):Abstract 4816 (2014).
Giuliano et al., "Circulating tumor cells as early predictors of metastatic spread in breast cancer patients with limited metastatic dissemination," Breast Cancer Res., 16(5):440 (2014).
Gross et al., "Abstract 3630: Non-enrichment based method for analysis of androgen receptor expression in circulating tumor cells (CTCs) in patients with metastatic castrate resistant prostate cancer," Proceedings: AACR 103rd Annual Meeting, Chicago, IL Mar. 31-Apr. 4, 2012, Retrieved from the Internet: URL:http://cancerres.aacrjournals.org/content/72/8_Supplement/3630 [retrieved on Jun. 13, 2017], 3 pages.
Guo et al., "A novel androgen receptor splice variant is up-regulated during prostate cancer progression and promotes androgen depletion-resistant growth," Cancer Res., 69(6):2305-2313 (2009).
Hao et al., "In vitro and in vivo prostate cancer metastasis and chemoresistance can be modulated by expression of either CD44 and CD147," PLoS One, 7(8):e40716 (2012).
Harada et al., "Androgen deprivation causes truncation of the C-terminal region of androgen receptor in human prostate cancer LNCaP cells," Cancer Sci., 103:1022-1027 (2012).
Isakoff et al., "TBCRC009: A Multicenter Phase II Clinical Trial of Platinum Monotherapy With Biomarker Assessment in Metastatic Triple-Negative Breast Cancer," J. Clin. Oncol., 33(17):1902-1909 (2015).
Kraan et al., "A new approach for rapid and reliable enumeration of circulating endothelial cells in patients," J. Thromb. Haemost., 10(5):931-939 (2012).
Krebs et al., "Analysis of circulating tumor cells in patients with non-small cell lung cancer using epithelial marker-dependent and -independenent approaches," J. Thorac Oncol., 7:306-315 (2012).
Kryzwinski et al., "Circos: an information aesthetic for comparative genomics," Genome Res., 19(9):1639-1645 (2009).
Larson et al., "Apoptosis of circulating tumor cells in prostate cancer patients," Cytometry, 62A:46-53 (2004).
Li et al., "Detection and validation of circulating endothelial cells, a blood-based diagnostic marker of acute myocardial infarction," PLoS One, 8(3):e58478 (2013).

(56) References Cited

OTHER PUBLICATIONS

Libertini et al., "Evidence for calpain-mediated androgen receptor cleavage as a mechanism for androgen independence," *Cancer Res.*, 67(19):9001-9005 (2007).

Lin et al., "A negative selection system PowerMag for effective leukocyte depletion and enhanced detection of EpCAM positive and negative circulating tumor cells," *Clinica Chem Acta*, 419:77-84(2013).

Marioni et al., "RNA-seq: an assessment of technical reproducibility and comparison with gene expression arrays," *Genome Res.*, 18(9):1509-1517 (2008).

Marquard et al., "Pan-cancer analysis of genomic scar signatures associated with homologous recombination deficiency suggests novel indications for existing cancer drugs," *Biomark Res.*, 3:9 (2015).

Mateo et al., "DNA-repair defects and olaparib in metastatic prostate cancer," *N. Engl. J. Med.*,373(18):1697-1708 (2015).

McDaniel et al., "Phenotypic diversity of circulating tumour cells in patients with metastatic castration-resistant prostate cancer," *BJU Int.*, 120(5B):E30-E44 (2017).

Melnikova et al., "Molecular characterizatoin of circulating tumor cells using a highly sensitive method of enrichment based on the CellSearch CTC profile kit," 22nd EORTC—NCI-AACR Symposium on Molecular Targets and Cancer; poster session, Jan. 1, 2010 (1 page).

Mercer, "Use of multiple markers to enhance clinical utility," *Immunol. Ser.*, 53:39-54 (1990).

Miyamoto et al., "Androgen receptor signaling in circulating tumor cells as a marker of hormonally responsive prostate cancer: supplemental methods single molecule sequencing and AR transcriptional signature," Retrieved from the internet: URL:http://http://cancerdiscovery.aacrjournals.org/content/suppl/2012/09/14/2159-8290.CD-12-0222.DC1. [retrieved on Apr. 16, 2019] DOI: 10.1158/2159-8290.CD-12-0222 (2012).

Mohamed et al., "Isolation of tumor cells using size and deformation," *J. Chromatogr. A.*, 1216(47):8289-8295 (2009).

Morin et al., "Application of massively parallel sequencing to microRNA profiling and discovery in human embryonic stem cells," *Genome Res.*, 18(4):610-621 (2008).

Morrison et al., "Labeling fluorescence in situ hybridization probes for genomic targets," in *Molecular Cytogenetics: Protocols and Applications*, Y.S. Fan Ed., Humana Press, Chapter 2, pp. 21-40 (2002).

Mortazavi et al., "Mapping and quantifying mammalian transcriptomes by RNA-Seq," *Nat. Methods*, 5(7):621-628 (2008).

Mumford et al., "Circulating melanoma cells in the diagnosis and monitoring of melanoma: an appraisal of clinical potential," *Mol. Diang. Ther.*, 18(2):175-183 (2014).

Nagy et al., "Mulitiplexed protein and gene profiling of circulating tumor cells (CTCs) in metastatic castration-resistant prostate cancer (mCRPC) using automated immunofluorescence and fluorescence in situ hybridization," *J. Clin. Oncol.*, 31(6):Suppl. 1, Abstract No. 158, (2013).

Paterlini-Brechot et al., "Circulating tumor cells (CTC) detection: clinical impact and future directions," *Cancer Lett.*, 253:180-204 (2007).

Pestana et al., Improved diffuse fluorescence flow cytometer prototype for high sensitivity detection of rare circulating cells in vivo, *J. Biomed. Optics*, 18(7):077002 (2013).

Phillips et al., "Physical biology in cancer. 2. The physical biology of circulating tumor cells," *Am. J. Physiol. Cell Physiol.*, 306(2):C80-C88 (2014).

Popova et al., "Ploidy and large-scale genomic instability consistently identify basal-like breast carcinomas with BRCA1/2 inactivation," *Cancer Res.*, 72(21):5454-5462 (2012).

Punnoose et al., "PTEN loss in circulating tumour cells correlates with PTEN loss in fresh tumour tissue from castration-resistant prostate cancer patients," *Br. J. Cancer*, 113(8):1226-1233 (2015).

Racila et al., "Detection and characterization of carcinoma cells in the blood," *Proc. Natl. Acad. Sci. USA*, 95(8):4589-4594 (1998).

Rathkopf et al., "Androgen receptor antagonists in castration-resistant prostate cancer," *Cancer J.*, 19(1):43-49 (2013).

Ren et al., "Detection of apoptotic circulating tumor cells in advanced pancreatic cancer following 5-fluorouracil chemotherapy," *Cancer Biol. Ther.*, 12(8):700-706 (2011).

Riethdorf et al., "Detection of circtulating tumor cells in peripheral blood of patients with metastatic breast cancer: a validation study of the CellSearch System," *Clin. Cancer Res.*, 13(3):920-928 (2007).

Robinson et al., "Integrative clinical genomics of advanced prostate cancer," *Cell*, 161(5):1215-1228 (2015).

Scher et al., "Association of AR-V7 on Circulating Tumor Cells as a Treatment-Specific Biomarker With Outcomes and Survival in Castration-Resistant Prostate Cancer," *JAMA Oncol.*, 2(11):1441-1449 (2016).

Scher et al., "Baseline CTC subtype to predict outcomes on mCRPC patients (pts) receiving enzalutamide (E) compared to abiraterone (A)," *J. Clin. Oncol.*, 35(Suppl.15):5070 (2017).

Scher et al., "Characterization of circulating tumor cells (CTCS) of metastatic castration resistant prostte cancer (MCRPC) patients in first, second & third line systemic therapies," *Annals Oncol.*, 25(Suppl. 4):iv58-iv84, Abstract 238P (2014).

Shaffer et al., "Circulating tumor cell analysis in patients with progressive castration-resistant prostate cancer," *Clin. Cancer Res.*, 13(7):2023-2029 (2007).

Sidaway, "Non-traditional CTCs indicate prognosis," *Nature Rev.*, 13(7):592 (2016).

Starlinger et al., "Discrimination between circulating endothelial cells and blood cell populations with overlapping phenotype reveals distinct regulation and predictive potential in cancer therapy," *Neoplasia*,13(10):980-990 (2011).

State of the Science Report, Highlights from the 19th Annual PCF Scientific Retreat, Oct. 2012, 21 pages.

Strijbos et al., "Circulating endothelial cells in oncology: pitfalls and promises," *Br. J. Cancer*, 98:1731-1735 (2008).

Tanaka et al., "Monoclonal antibody targeting of N-cadherin inhibits prostate cancer growth, metastasis and castration resistance," *Nat. Med.*, 16(12):1414-1420 (2010).

Theodoropoulo et al., "Circulating tumor cells with a putative stem cell phenotype in peripheral blood of patients with breast cancer," *Cancer Letts.*, 288:99-106 (2010).

Tockman et al., "Considerations in bringing a cancer biomarker to clinical application," *Cancer Res.*, 52:2711s-2718s (1992).

Tufman et al., "Biological markers in lung cancer: A clinician's perspective," *Cancer Biomarkers*, 6(3-4):123-135 (2009).

Ulmer et al., "Immunomagnetic enrichment, genomic characterization, and prognostic impact of circulating melanoma cells," *Clin. Cancer Res.*, 15(2):531-537 (2004).

Vollebergh et al., "Genomic patterns resembling BRCA1- and BRCA2-mutated breast cancers predict benefit of intensified carboplatin-based chemotherapy," *Breast Cancer Res.*, 16(3):R47 (2014).

Wang et al., "Identification and characterization of circulating prostate carcinoma cells," *Cancer*, 88(12):2787-2795 (2000).

Watkins et al., "Genomica scars as biomarkers of homologous recombination deficiency and drug response in breast and ovarian cancers," *Breast Cancer Res.*, 16(3):211 (2014).

Werner et al., "Analytical Validation and Capabilities of the Epic CTC Platform: Enrichment-Free Circulating Tumour Cell Detection and Characterization," *J. Circ. Biomark.*, 4:3 (2015).

Wong et al., "Evolution of androgen receptor targeted therapy for advanced prostate cancer," *Nat. Rev. Clin. Oncol.*, 11:365-376 (2014).

Woywodt et al., "Isolation and enumeration of circulating endothelial cells by immnomagnetic isolation: proposal of a definition and a consensus protocol," *J. Thromb. Heaemost.*, 4:671-677 (2006).

Zafarana et al., "Copy number alterations of c-MYC and PTEN are prognostic factors for relapse after prostate cancer radiotherapy," *Cancer*, 118(16):4053-4062 (2012).

Zhao et al., CN 101226118 b, machine translation to English, 2010, 22 pages.

Zhau et al., "Epithelial to mesenchymal transition (EMT) in human prostate cancer: lessons learned from ARCaP model," *Clin. Exp. Metastasis*, 25(6):601-610 (2008).

(56) References Cited

OTHER PUBLICATIONS

Damani et al., "Characterization of circulating endothelial cells in acute myocardial infarction," Sci. Tranl. Med., 4(126):126ra33 (2012).
Danila et al., "TMPRSS2-ERG status in circulating tumor cells as a predictive biomarker of sensitivity in castration-resistant prostate cancer patients treated with abiraterone acetate," Eur. Urol., 60(5):897-904 (2011).
De Giorgi et al., "Application of a filtration- and isolation-by-size technique for the detection of circulating tumor cells in cutaneous melanoma," J. Invest. Dermatol., 130:2440-2447 (2010).
Evans et al., "Noninvasive measurement of androgen receptor signaling with a positron-emitting radiopharmaceutical that targets prostate-specific membrane antigen," Proc. Natl. Acad Sci. USA, 108(23):9578-9582 (2011).
Guo et al., "A new trick of an old molecule: androgen receptor splice variants taking the stage?!," Int. J. Bio. Sci., 7(6):815-822 (2011).
Jiang et al., "A comparison of isolated circulating tumor cells and tissue biopsies using whole-genome sequencing in prostate cancer," Oncotarget, 6(42):44781-44793 (2015).
Jiang et al., "Detection of androgen receptor mutations in circulating tumor cells in castration-resistant prostate cancer," Clin. Chem., 56(9):1492-1495 (2010).
Jilaveanu et al., "PD-L1 expression in clear cell renal cell carcinoma: an analysis of nephrectomy and sites of metastases," J. Cancer, 5(3):166-172 (2014).
Kodiha et al., "Computer-based fluorescence quantification: a novel approach to study nucleolar biology," BMC Cell Biol., 12:25, 1-18 (2011).
Lin et al., "Disseminated and circulating tumor cells: Role in effective cancer management," Crit. Rev. Oncol. Hematol., 77(1):1-11 (2011).
Lu et al., "Parylene membrane slot filter for the capture, analysis and culture of viable circulating tumor cells," IEEE 23rd International Conference, Piscataway, NJ, Jan. 24, 2010, pp. 935-938.
Ma et al., "Potent antitumor activity of an auristatin-conjugated, fully human monoclonal antibody to prostate-specific membrane antigen," Clin. Cancer Res., 12(8):2591-2596 (2006).
Marrinucci et al., "Bronchioloalveolar lung CTCs retain cytomorphologic features of primary tumor type," J. Clin. Oncol., 26(15S):19118 (2008).
Mostaghel et al., "Molecular pathways: targeting resistance in the androgen receptor for therapeutic benefit," Clin. Cancer Res., 20(4):791-798 (2014).
Stanbrough et al., "Prostatic intraepithelial neoplasia in mice expressing an androgen receptor transgene in prostate epithelium," Proc. Natl. Acad. Sci USA, 98(19):10823-10828 (2001).
Stott et al., "Isolation of circulating tumor cells using a microvortex-generating herringbone-chip," Proc. Natl. Acad. Sci. USA, 107(43):18392-18397 (2010).
Vona et al., "Enrichment, immunomorphological, and genetic characterization of fetal cells circulating in maternal blood," Am. J. Pathol., 160(1):51-58 (2002).
Yu et al., "Circulating tumor cells: approaches to isolation and characterization," J. Cell Biol., 192(3):373-382 (2011).
Zheng et al., "Level of circulating PD-L1 expression in patients with advanced gastric cancer and its clinical implications," Chin. J. Cancer Res., 26(1):104-111 (2014).
Zheng et al., "Membrane microfilter device for selective capture, electrolysis and genomic analysis of human circulating tumor cells," J. Chromatogr., 1162(2):154-161 (2007).

\* cited by examiner

| Pts Characteristics | N=41 |
|---|---|
| Age, y |  |
| Median | 70 |
| Range | 40-82 |
| Sites of metastases |  |
| Bone | 39 (95%) |
| Nodal | 28 (68%) |
| Visceral | 13 (32%) |
| ECOG PS |  |
| 0 | 6 (15%) |
| 1 | 33 (80%) |
| 2 | 2 (5%) |
| NA | 1 (2%) |

| Previous treatments | N=41 |
|---|---|
| Number of previous lines for CRPC |  |
| Median | 3 |
| Range | 1-5 |
| Previous therapies |  |
| Bicalutamide | 41 (100%) |
| Docetaxel | 26 (63%) |
| Cabazitaxel | 4 (10%) |
| Abiraterone (AA) | 14 (34%) |
| Enzalutamide (E) | 3 (7%) |
| Investigational agents | 13 (32%) |

Figure 1B

| Events | CRPC N=41 | HV N=10 |
|---|---|---|
| Traditional CTC | | |
| Median | 5 | 0 |
| Range | 0-98 | 0 |
| CK- cells | | |
| Median | 3 | 0 |
| Range | 0-48 | 0 |
| Apoptotic cells | | |
| Median | 4 | 0 |
| Range | 0-92 | 0 |
| Small nuclear size | | |
| Median | 1 | 0 |
| Range | 0-16 | 0 |

Figure 2A

| AR expression | |
|---|---|
| Traditional CTC | |
| Avg AR intensity | 3.71 (0-16.80) |
| % AR positive | Median 33% (0-100%) |
| CK- cells | |
| % AR positive | XXX (range XX) |
| Apoptotic cells | XXX |
| Small nuclear size | XXX |

Figure 2B

| Patient Characteristics | N=41 | Previous treatments | N=41 |
|---|---|---|---|
| Age, yr | | Number of previous lines for CRPC | |
| Median | 70 | Median | 3 |
| Range | 40-82 | Range | 1-5 |
| Sites of metastases | | Previous therapies | |
| Bone | 39 (95%) | Bicalutamide | 41 (100%) |
| Nodal | 28 (68%) | Docetaxel | 26 (63%) |
| Visceral | 13 (32%) | Cabazitaxel | 4 (10%) |
| | | Abiraterone (AA) | 14 (34%) |
| ECOG PS | | Enzalutamide (E) | 3 (7%) |
| 0 | 6 (15%) | Investigational agents | 13 (32%) |
| 1 | 33 (80%) | | |
| 2 | 2 (5%) | | |
| Healthy Volunteer Characteristics | N=20 | Healthy Volunteer Characteristics | N=20 |
| Age, yr | | Sex | |
| Median | | Male | |
| Range | | Female | |

| Patient # | Cell Type | # Cells evaluated PTEN | % AR+ | PTEN heterozygous (HE) | PTEN homozygous (HO) | % Cells PTEN deletions |
|---|---|---|---|---|---|---|
| 2* | Traditional CTCs | 7 | 14% | 2 | 0 | 28.6% |
|  | CK- | 0 | - | - | - | - |
|  | Small | 0 | - | - | - | - |
| 9 | Traditional CTCs | 32 | 0% | 1 | 0 | 3.1% |
|  | CK- | 4 | 25% | 0 | 0 | 0.0% |
|  | Small | 1 | 0% | 0 | 0 | 0.0% |
| 12* | Traditional CTCs | 11 | 36% | 0 | 4 | 36.4% |
|  | CK- | 9 | 44% | 1 | 4 | 55.6% |
|  | Small | 2 | 0% | 0 | 0 | 0.0% |
| 40 | Traditional CTCs | 13 | 0% | 0 | 0 | 0.0% |
|  | CK- | 0 | - | - | - | - |
|  | Small | 0 | - | - | - | - |
| 35 | Traditional CTCs | 12 | 0% | 1 | 1 | 16.7% |
|  | CK- | 5 | 0% | 0 | 0 | 0.0% |
|  | Small | 0 | - | - | - | - |

False positive rate in WBCs: PTEN HE=2.5% (3/120); PTEN HO=0% (0/120)

Figure 12B

| Patient # | Cell Type | # Cells evaluated ERG | % AR+ | ERG insertion | ERG deletion | % Cells ERG rearranged |
|---|---|---|---|---|---|---|
| 5 | Traditional CTCs | 11 | 0%** | 0 | 0 | 0.0% |
|  | CK- | 0 | - | - | - | - |
|  | Small | 0 | - | - | - | - |
| 7* | Traditional CTCs | 39 | 74% | 1 | 2 | 7.7% |
|  | CK- | 9 | 89% | 0 | 0 | 0.0% |
|  | Small | 11 | 27% | 2 | 1 | 27.3% |
| 23* | Traditional CTCs | 64 | 94% | 4 | 0 | 6.3% |
|  | CK- | 6 | 83% | 1 | 0 | 16.7% |
|  | Small | 0 | - | - | - | - |

False positive rate in WBCs: ERG insertion=3.3% (2/60); ERG deletion=0% (0/60)

*additional slides beyond the standard 2-slide test were evaluated for FISH
**3 cells unevaluable for AR expression

CIRCULATING TUMOR CELL DIAGNOSTICS FOR PROSTATE CANCER BIOMARKERS

This application claims the benefit of priority of U.S. provisional application Ser. No. 61/932,096, filed Jan. 27, 2014, the entire contents of which are incorporated herein by reference.

The present disclosure relates generally to methods for identification and molecular characterization of CTC subpopulations associated with castration-resistant prostate cancer (CRPC).

BACKGROUND

Prostate cancer is the most commonly diagnosed solid organ malignancy in the United States (US) and remains the second leading cause of cancer deaths among American men. In 2014 alone, the projected incidence of prostate cancer is 233,000 cases with deaths occurring in 29,480 men, making metastatic prostate cancer therapy truly an unmet medical need. Siegel et al., 2014. CA Cancer J Clin. 2014; 64(1):9-29. Epidemiological studies from Europe show comparable data with an estimated incidence of 416700 new cases in 2012, representing 22.8% of cancer diagnoses in men. In total, 92 200 PC-specific deaths are expected, making it one of the three cancers men are most likely to die from, with a mortality rate of 9.5%.

Despite the proven success of hormonal therapy for prostate cancer using chemical or surgical castration, most patients eventually will progress to a phase of the disease that is metastatic and shows resistance to further hormonal manipulation. This has been termed metastatic castration-resistant prostate cancer (mCRPC). Despite this designation, however, there is evidence that androgen receptor (AR)-mediated signaling and gene expression can persist in mCRPC, even in the face of castrate levels of androgen. This may be due in part to the upregulation of enzymes involved in androgen synthesis, the overexpression of AR, or the emergence of mutant ARs with promiscuous recognition of various steroidal ligands. Treatment of patients with mCRPC remains a significant clinical challenge.

Prior to 2004, there was no treatment proven to improve survival for men with mCRPC. The treatment of patients with mitoxantrone with prednisone or hydrocortisone was aimed only at alleviating pain and improving quality of life, but there was no benefit in terms of overall survival (OS). In 2004, the results of two major phase 3 clinical trials, TAX 327 and SWOG (Southwest Oncology Group) 9916, established Taxotere® (docetaxel) as a primary chemotherapeutic option for patients with mCRPC. Additional hormonal treatment with androgen receptor (AR) targeted therapies, chemotherapy, combination therapies, and immunotherapy, has been investigated for mCRPC, and recent results have offered additional options in this difficult-to-treat patient group. With the advent of exponential growth of novel agents tested and approved for the treatment of patients with metastatic castration-resistant prostate cancer (mCRPC) in the last 5 years alone, issues regarding the optimal sequencing or combination of these agents have arisen. Several guidelines exist that help direct clinicians as to the best sequencing approach and most would evaluate presence or lack of symptoms, performance status, as well as burden of disease to help determine the best sequencing for these agents. Mohler et al., 2014, J Natl Compr Canc Netw. 2013; 11(12):1471-1479; Cookson et al., 2013, J Urol. 2013; 190(2):429-438. Currently, approved treatments consist of taxane-class cytotoxic agents such as Taxotere® (docetaxel) and Jevtana® (cabazitaxel), and anti-androgen hormonal therapy drugs such as Zytiga® (arbiterone, blocks androgen production) or Xtandi® (enzalutamide, an androgen receptor (AR) inhibitor).

The challenge for clinicians is to decide the best sequence for administering these therapies to provide the greatest benefit to patients. However, therapy failure remains a significant challenge based on heterogeneous responses to therapies across patients and in light of cross-resistance from each agent. Mezynski et al., Ann Oncol. 2012; 23(11):2943-2947; Noonan et al., Ann Oncol. 2013; 24(7):1802-1807; Pezaro et al., Eur Urol. 2014, 66(3): 459-465. In addition, patients may lose the therapeutic window to gain substantial benefit from each drug that has been proven to provide overall survival gains. Hence, better methods of identifying the target populations who have the most potential to benefit from targeted therapies remain an important goal.

Circulating tumor cells (CTCs) represent a significant advance in cancer diagnosis made even more attractive by their non-invasive measurement. Cristofanilli et al., N Engl J Med 2004, 351:781-91. CTCs released from either a primary tumor or its metastatic sites hold important information about the biology of the tumor. Historically, the extremely low levels of CTCs in the bloodstream combined with their unknown phenotype has significantly impeded their detection and limited their clinical utility. A variety of technologies have recently emerged for detection, isolation and characterization of CTCs in order to utilize their information. CTCs have the potential to provide a non-invasive means of assessing progressive cancers in real time during therapy, and further, to help direct therapy by monitoring phenotypic physiological and genetic changes that occur in response to therapy. In most advanced prostate cancer patients, the primary tumor has been removed, and CTCs are expected to consist of cells shed from metastases, providing a "liquid biopsy." While CTCs are traditionally defined as EpCAM/cytokeratin positive (CK+) cells, CD45−, and morphologically distinct, recent evidence suggests that other populations of CTC candidates exist including cells that are EpCAM/cytokeratin negative (CK−) or cells smaller in size than traditional CTCs. These findings regarding the heterogeneity of the CTC population, suggest that enrichment-free CTC platforms are favorable over positive selection techniques that isolate CTCs based on size, density, or EpCAM positivity that are prone to miss important CTC subpopulations.

CRPC presents serious challenges to both the patients suffering from this advanced form of PrCa and the clinicians managing these patients. Clinicians are often faced with providing comprehensive diagnoses and assessments of the mechanisms that cause disease progression in an effort to guide appropriate and individualized treatments. By identifying appropriate therapeutic and prognostic markers, the potential clinical benefit of targeted therapy is increased, and clinicians are enabled to better managed CRPC, improve the QOL for patients, and enhance clinical outcomes. A need exists to develop accurate and non-invasive methods for detecting the emergence and monitoring mCRPC. The present invention addresses this need by providing biomarker signatures characteristic of CTC subpopulations associated with CRPC based on a robust CTC detection and characterization platform that enables the phenotypic characterization of CTCs. Related advantages are provided as well.

SUMMARY

The present invention provides methods for diagnosing CRPC in a patient afflicted with prostate cancer.

The present invention provides a method for detecting CRPC in a patient afflicted with prostate cancer comprising (a) performing a direct analysis comprising immunofluorescent staining and morphological characterization of nucleated cells in a blood sample obtained from the patient to detect circulating tumor cells (CTC), (b) determining prevalence of a CTC subpopulation associated with CRPC comprising detecting a measurable feature of each biomarker in a panel of morphological and protein biomarkers, and (c) comparing the prevalence of said CTC subpopulation to a predetermined threshold value, wherein the prevalence of the CTC subpopulation associated with CRPC above said predetermined threshold value is indicative of CRPC. In some embodiments, the CTC subpopulation associated with CRPC comprises CK− CTCs. In some embodiments, the CTC subpopulation associated with CRPC comprises small CTCs. In some embodiments, the direct analysis in step (a) detects CTCs selected from the group consisting of traditional CTCs, cytokeratin negative (CK⁻) CTCs, small CTCs, and CTC clusters.

In some embodiments, the CRPC is mCRPC. In some embodiments, the morphological characteristics of CTCs comprise one or more of the group consisting of nucleus size, nucleus shape, presence of holes in nucleus, cell size, cell shape and nuclear to cytoplasmic ratio, nuclear detail, nuclear contour, prevalence of nucleoli, quality of cytoplasm and quantity of cytoplasm. In some embodiments, the immunofluorescent staining of nucleated cells comprises pan cytokeratin (CK), cluster of differentiation (CD) 45, and diamidino-2-phenylindole (DAPI). In some embodiments, the immunofluorescent staining of nucleated cells further comprises Androgen Receptor (AR).

In some embodiments, the disclosed methods for detecting CRPC in a patient afflicted with prostate cancer further comprise molecular characterization of the CTCs. In related embodiments, the molecular characterization comprises fluorescence in situ hybridization (FISH). In further embodiments, the FISH detects rearrangement of erythroblast transformation-specific (ETS)-related gene (ERG) and/or loss of Phosphatase and tensin homolog gene (PTEN).

The invention also provides a method for detecting CRPC in a patient afflicted with prostate cancer comprising (a) performing a direct analysis comprising immunofluorescent staining and morphological characterization of nucleated cells in a blood sample obtained from the patient to detect circulating tumor cells (CTC), (b) determining prevalence of a CTC subpopulation associated with CRPC comprising detecting a measurable feature of each biomarker in a panel of morphological and protein biomarkers, (c) comparing the prevalence of said CTC subpopulation to a predetermined threshold value, wherein the prevalence of the CTC subpopulation associated with CRPC above said predetermined threshold value is indicative of CRPC, and (c) repeating steps (a) through (c), wherein an increase in the prevalence of the CTC population associated with CRPC indicates progression of prostate cancer to CRPC. In some embodiments, the patient is undergoing primary androgen deprivation therapy (ADT). In some embodiments, the increase in the prevalence of the CTC population associated with CRPC predicts resistance to androgen deprivation therapy (ADT). In some embodiments, the increase in the prevalence of the CTC population associated with mCRPC informs a subsequent decision to initiate secondary hormonal therapy directed at AR inhibition.

BRIEF DESCRIPTION OF THE DRAWINGS

The patent or application file contains at least one drawing executed in color. Copies of this patent or patent application publication with color drawing(s) will be provided to the Office upon request and payment of the necessary fee.

FIGS. 1A and 1B, show methods relating to performing the embodiments described herein and describes the exemplified study population. FIG. 1A shows a schematic of a representative CTC collection and detection process: (1) nucleated cells from blood sample placed onto slides; (2) slides stored in −80° C. biorepository; (3) slides stained with CK, CD45, DAPI and AR; (4) slides scanned; (5) multi-parametric digital pathology algorithms run; (6) software and human reader confirmation of CTCs and quantitation of biomarker expression; (7) for FISH, coordinates are recorded and coverslip removed; (8) FISH assay is run; (9) regional WBCs are scored to assess normal; and (10) CTCs relocated and scored. FIG. 1B shows information on the study population. Demographic and clinical characteristics of patients at the time of inclusion in the study are shown in the left and right panels. Forty one progressing CRPC patients (pts) and 10 healthy volunteer (HV) were included in the study.

FIGS. 2A-2C show further methods relating to performing the embodiments described herein and identification of novel CTC populations. FIG. 2A shows the number of CTCs and other CTCs subpopulations detected in 1 mL of blood. FIG. 2B shows AR expression in CTC population. FIG. 2C shows identification of novel CTC subpopulations. Examples of traditional, small, and CK− CTCs found in patient samples are shown. CK− CTCs and small CTCs with cancer related morphology and expression of AR proteins were identified.

FIG. 3A shows FISH analysis, which was performed on patient samples where small and CK− cells were identified by IF. Panel A shows ERG insertion in small CTC; panel B shows 5' ERG deletion in small CTC; panel C shows 5' ERG deletion in small CTC; panel D shows 5' ERG deletion in CK− CTC; panel E shows ERG insertion in CK− CTC; panel F shows PTEN deletion in CK− CTC. FIG. 3B shows nuclear size per CTC as calculated by Epic software for each patient. 1.9 million normal WBCs were used to calculate the WBC mean and standard deviation. Green (upper) and black (lower) dashed lines indicate WBC size cutoffs equal to one standard deviation from the mean. Red (middle) dashed line shows mean WBC size. CTCs with nuclear size smaller than or within one standard deviation of the WBC mean are likely to be missed with size or density selection. FIG. 3C shows percentage of cells with different nuclear sizes for each patient. The percentage of cells for each patient with nuclear size greater than one standard deviation from the WBC mean (green, upper in bar graph; nuclear size>67 µm²), within one standard deviation of the mean (red, middle in bar graph; nuclear size 39-67 µm²) and less than one standard deviation from the mean (black, lower in bar graph; nuclear size<39 µm²). Cells represented in black and red are likely to be missed with size or density selection. FIG. 3D shows the incidence of CK− CTC subpopulations. The upper left panel shows CK intensity per CTC per patient. Dashed line at 2.8 indicates cutoff for CK positivity. Cells with CK below 2.8 are detected based on abnormal morphology and AR positivity. The upper right panel shows the percentage of cells for each patient with CK+(red, lower in bar graph) or CK− (black, upper in bar graph) CTCs. The lower panel shows additional information on the CTC subpopulations.

Figure 4A:
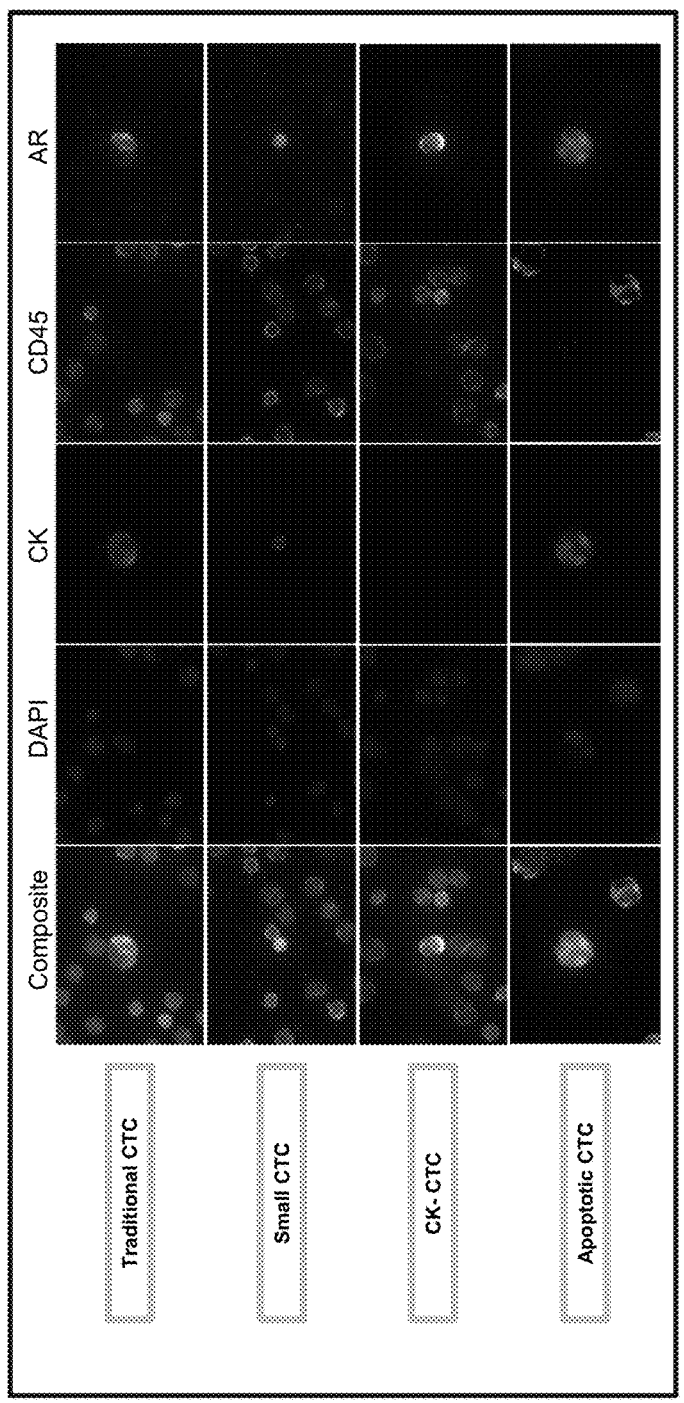
Figure 4B:
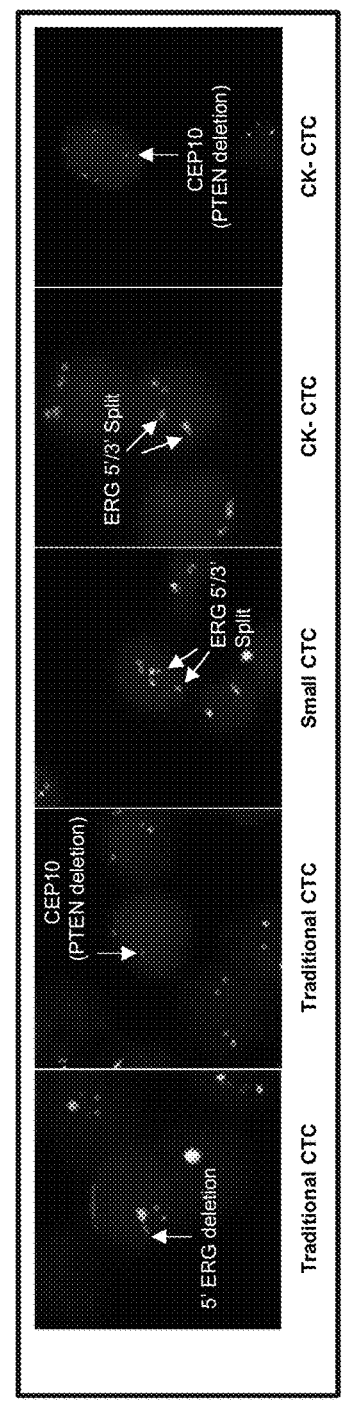

FIGS. 4A and 4B show that patients with mCRPC harbor traditional and non-traditional CTCs with prostate cancer alterations. Representative IF images and examples of PTEN deletions and/or ERG rearrangements found in traditional and non-traditional CTCs in mCRPC patient samples. FIG. 4A shows IF images of traditional (DAPI+/CD45−/CK+/abnormal morphology), small (DAPI+/CD45−/CK+/small nuclear size), CK− (DAPI+/CD45−/CK−/AR+/abnormal morphology), and apoptotic (DAPI+/CD45−/CK+/nuclear disintegration/abnormal morphology) CTCs from mCRPC patient samples are shown. FIG. 4B shows examples of ERG and PTEN alterations detected by FISH in traditional and non-traditional CTCs from mCRPC patient samples. ERG rearrangements can occur by deletion (resulting in loss of 5' signal; far let panel) or insertion (resulting in split signals; center and second from left panel).

Figure 5:
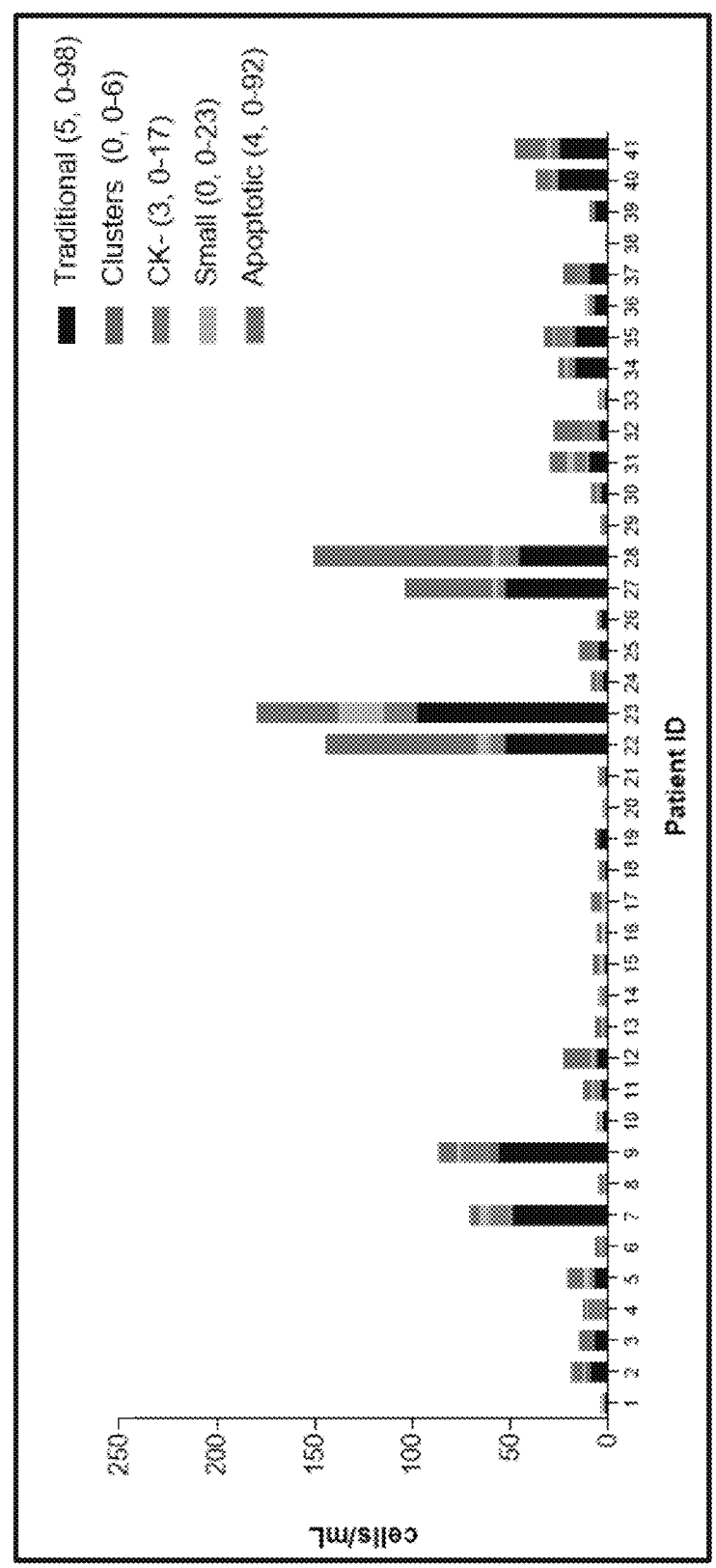

FIG. 5 shows that the proportion of traditional and non-traditional CTCs vary greatly across mCRPC patient samples. Traditional and non-traditional CTCs/mL of blood per mCRPC patient. Cohort median counts/mL and range for each CTC subpopulation are included in the legend (shown in bar graphs from bottom to top, as found: traditional, clusters, CK−, small, apoptotic).

Figures 6A, 6B:
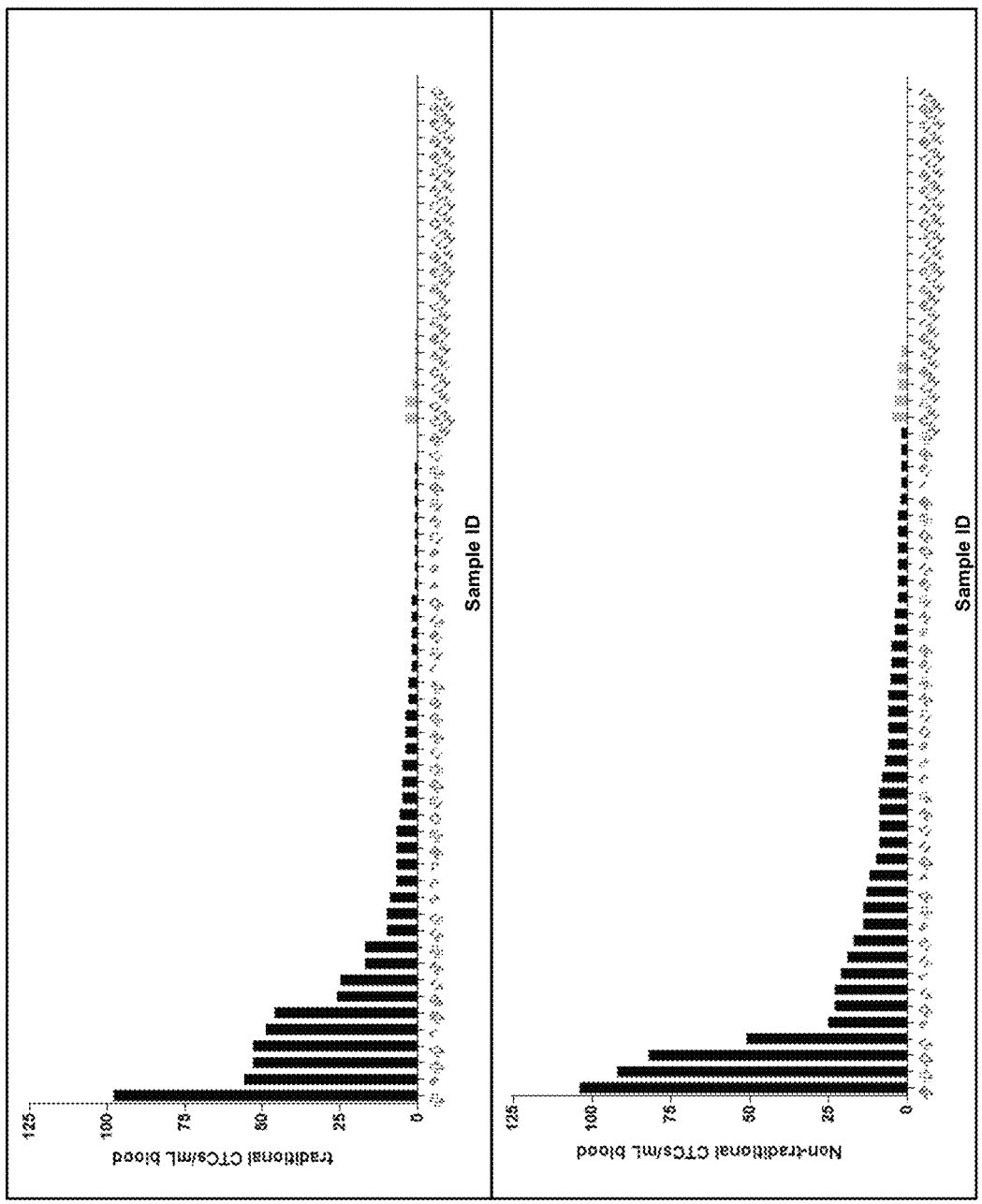

FIGS. 6A and 6B show traditional and non-traditional CTCs/mL in mCRPC patient and healthy volunteer (HV) samples. FIG. 6A show traditional CTCs/mL blood identified in mCRPC patient samples (black, left) and HV samples (blue, right). FIG. 6B shows non-traditional CTCs/mL blood identified in patient samples (black, left) and HV samples (blue, right).

Figure 7A:
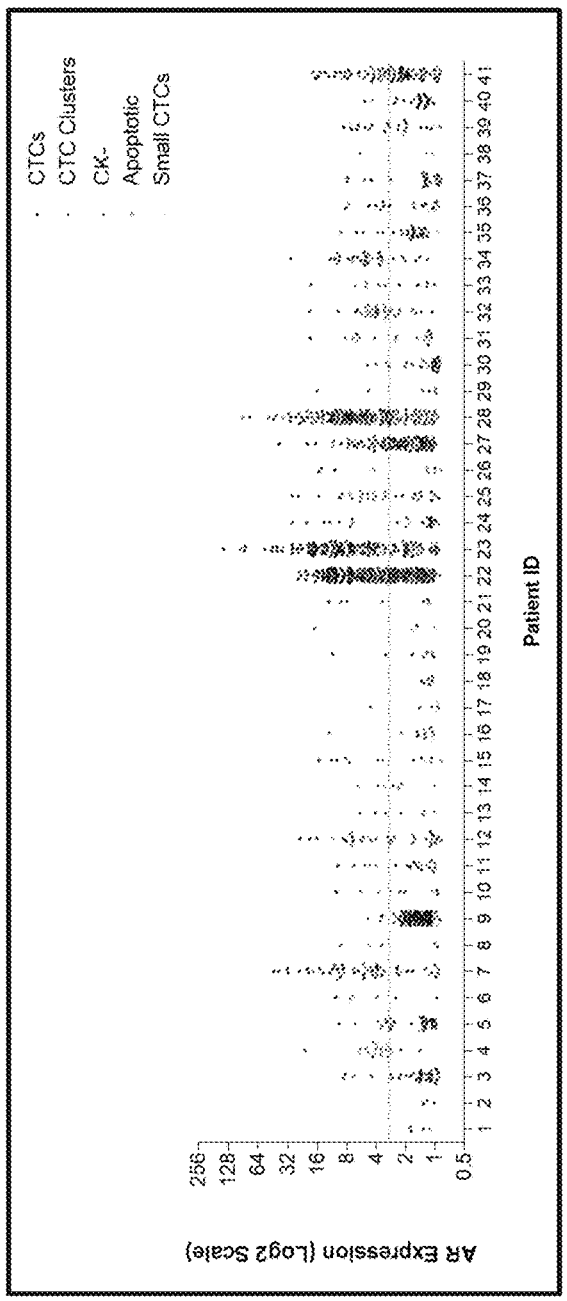
Figure 7B:
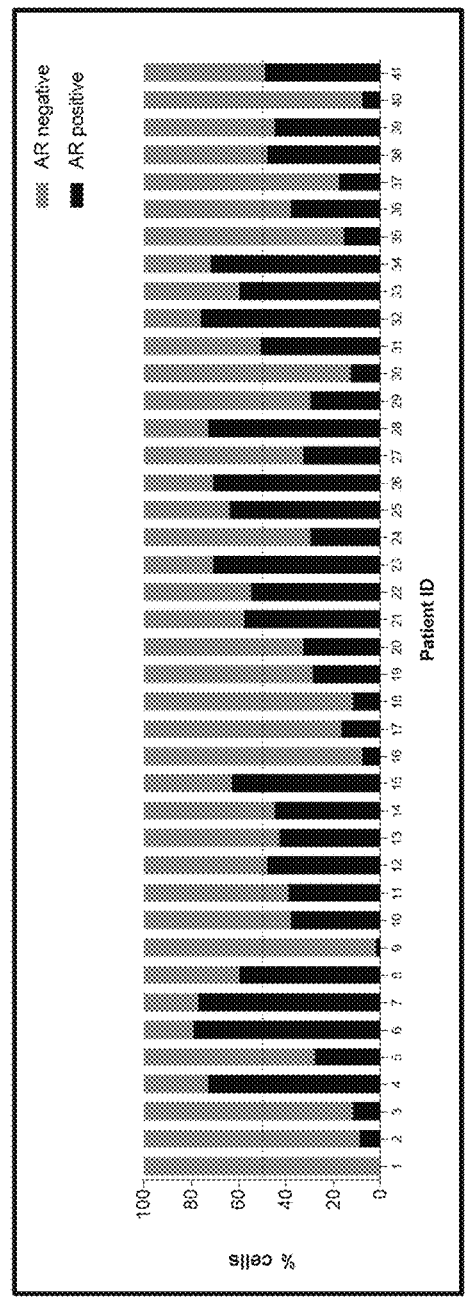

FIGS. 7A and 7B show AR expression varies across traditional and non-traditional CTCs in mCRPC patient samples. FIG. 7A shows AR expression per patient as detected with a standard 2-slide test. The dashed line at 3 indicates the cutoff for AR positivity. FIG. 7B shows the percentage of AR positive (lower in bar graph) and AR negative (upper in bar graph) CTCs/mL (traditional and non-traditional) per patient. The dashed line indicates 50%.

Figure 8A:
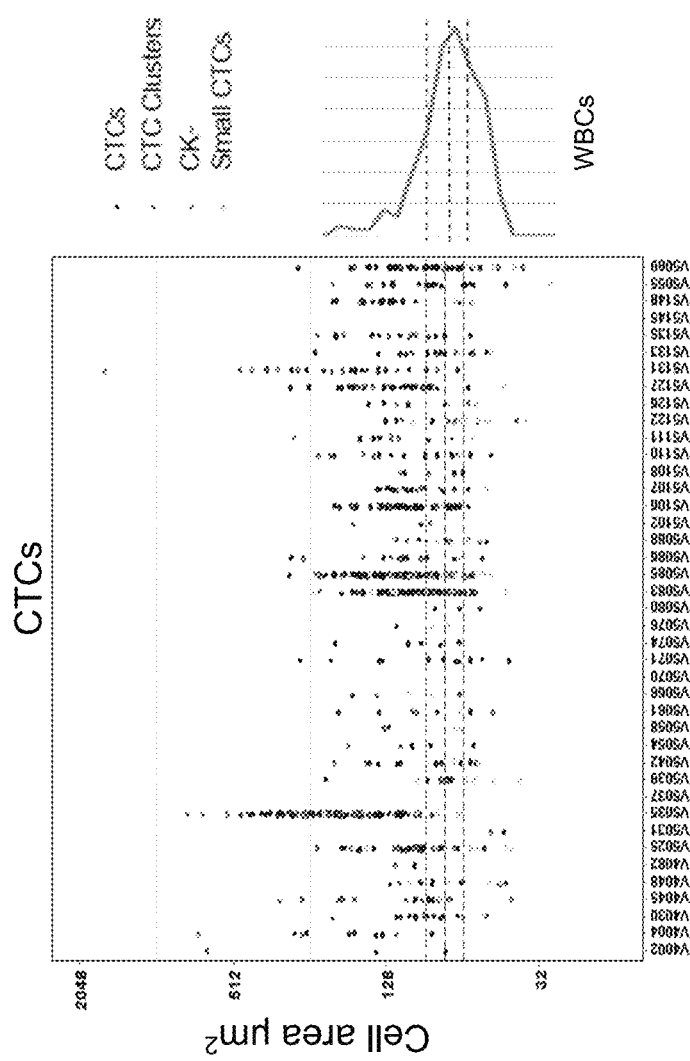
Figure 8B:
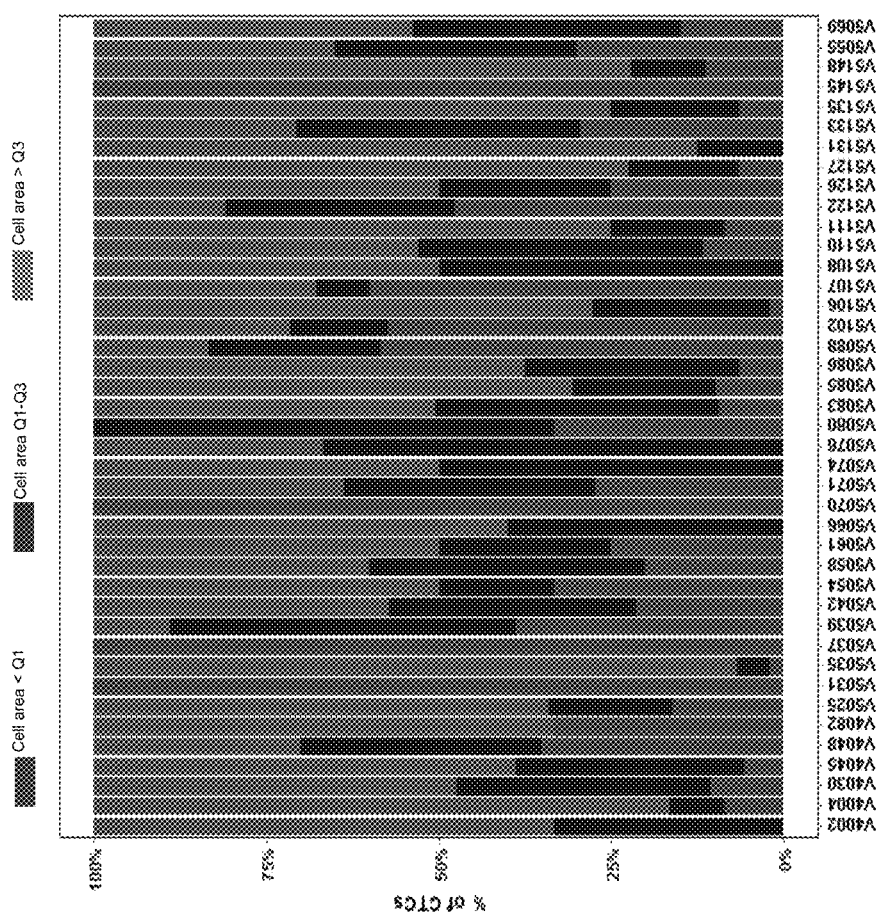

FIGS. 8A and 8B show CTC size varies greatly across mCRPC samples. FIG. 8A shows cellular area per CTC as calculated by Epic software for each patient. Dots are color coded by traditional and non-traditional CTC subtypes (as classified by trained scorers). WBC frequency distribution curve was generated by measuring the cellular area of approximately 300 normal WBCs. The blue (middle) dashed line represents the median WBC area. Red (lower) and green (upper) dashed lines indicate WBC size cutoffs equal to the 25th and 75th percentile, respectively. FIG. 8B shows the percentage of cells for each patient with CTC area greater than the WBC 75th percentile (green, right bar at top, upper in bar graph), within the WBC interquartile range (blue, middle bar at top, middle in bar graph), and less than the WBC 25th percentile (red, left bar at top, lower in bar graph). Cells represented in blue and red are similar in size to WBCs and are likely to be missed by CTC platforms using size or density selection.

Figure 9A:
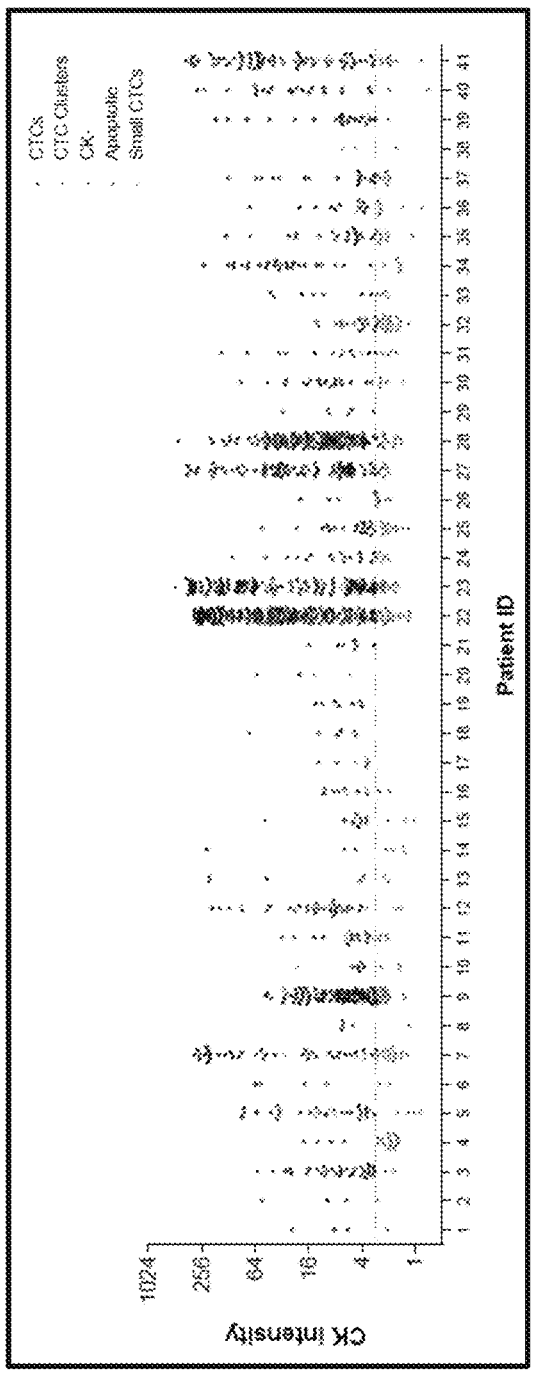
Figure 9B:
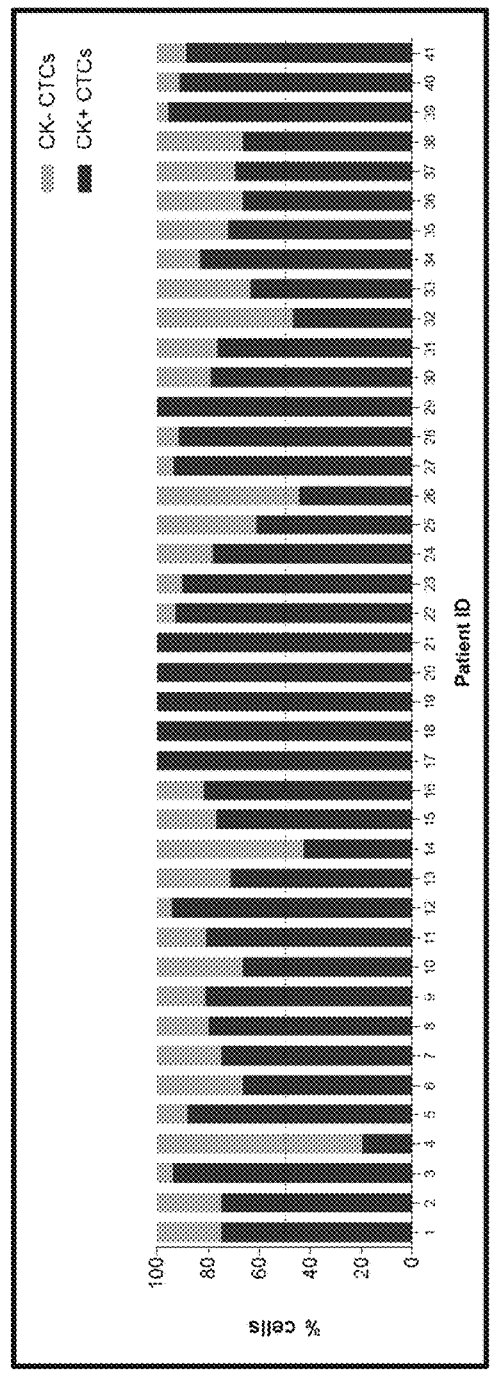

FIGS. 9A and 9B show CK expression varies across traditional and non-traditional CTC subtypes in patients with mCRPC. FIG. 9A shows CK intensity distribution across traditional and non-traditional CTCs per patient as detected with a standard 2-slide test. The dashed line at 2.8 indicates the cutoff for CK positivity. FIG. 9B shows percentage of CK positive (lower in bar graph) and CK negative (upper in bar graph) CTCs (traditional and non-traditional) per patient as detected with a standard 2-slide test. The dashed line indicates 50%.

Figure 10:
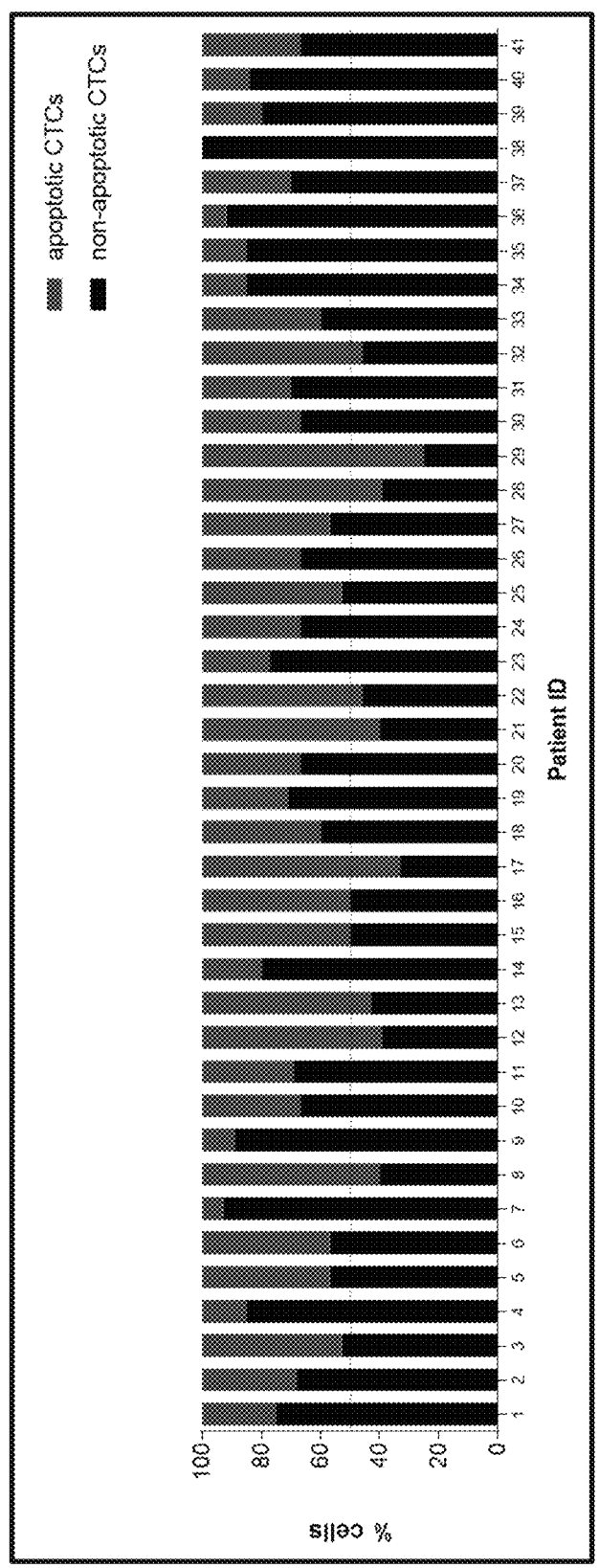

FIG. 10 shows apoptotic CTCs are frequently detected in patients with mCRPC. Percentage of non-apoptotic (lower in bar graph) and apoptotic (upper in bar graph) CTCs/mL per patient; 9 patients had predominantly apoptotic CTCs. The dashed line indicates 50%.

FIG. 11 shows demographic and clinical characteristics of patients and healthy volunteers at the time of inclusion in the study.

FIGS. 12A and 12B show results of FISH analysis performed on select patients. The percentage of CTCs (stratified by CTC type) with AR positivity by IF is given for patients assessed for A) PTEN loss or B) ERG rearrangement by FISH. FIG. 12A shows the number of assessed CTCs with PTEN heterozygous (HE) or homozygous (HO) loss and the total percentage of CTCs with PTEN loss is given. FIG. 12B shows the number of assessed CTCs with ERG rearrangement by insertion or deletion and the total percentage of CTCs with ERG rearrangement is indicated.

DETAILED DESCRIPTION OF THE INVENTION

The present disclosure is based, in part, on the unexpected discovery that phenotypic characterization of CTCs obtained from prostate cancer patients can identify subpopulations of CTCs that are associated with CRPC based on diagnostic biomarker signatures. In particular, as disclosed herein, the biomarkers associated with a CTC subpopulation associated with CRPC comprise CK− CTCs and/or small CTCs. The phenotypic and genetic characterization of all circulating nucleated cells as described herein identified the frequent presence of heterogeneous non-traditional CTC populations in mCRPC.

Despite the proven success of hormonal therapy for prostate cancer using chemical or surgical castration, most patients eventually will progress to a phase of the disease that is metastatic and shows resistance to further hormonal manipulation. This has been termed mCRPC. Despite castrate levels of androgens, the androgen receptor (AR) remains active and continues to drive prostate cancer progression. This understanding has led to the development of anti-androgen hormonal therapy drugs such as, for example, Zytiga (arbiterone, blocks androgen production) and Xtandi (enzalutamide, an AR inhibitor), which are beneficial in extending lives of CRPC patients. Significantly, the methods disclosed herein enable detection of CRPC in a patient afflicted with prostate cancer and make it possible to identify different patient groups in the resistance setting in order to tailor subsequent treatment more precisely and effectively. In related embodiments, the methods allow for resistance monitoring of a prostate cancer patients by enabling detection of an emergence of CRPC or mCRPC in a patient afflicted with prostate cancer.

In one aspect, the present invention describes a method for detecting castrate-resistant prostate cancer (CRPC) in a patient afflicted with prostate cancer comprising (a) performing a direct analysis comprising immunofluorescent staining and morphological characterization of nucleated cells in a blood sample obtained from the patient to detect circulating tumor cells (CTC), (b) determining prevalence of a CTC subpopulation associated with CRPC comprising detecting a measurable feature of each biomarker in a panel of morphological and protein biomarkers, and (c) comparing the prevalence of said CTC subpopulation to a predetermined threshold value, wherein the prevalence of the CTC subpopulation associated with CRPC above said predetermined threshold value is indicative of CRPC. In additional embodiments, the CRPC is metastatic mCRPC.

In some embodiments, the CTC subpopulation associated with mCRPC comprises CK− CTCs. In additional embodiments, the subpopulation associated with mCRPC comprises small CTCs. In some embodiments, the direct analysis in step (a) detects CTCs selected from the group consisting of traditional CTCs, cytokeratin negative (CK−) CTCs, small CTCs, and CTC clusters.

In some embodiments, the morphological characteristics of CTCs comprise one or more of the group consisting of nucleus size, nucleus shape, presence of holes in nucleus, cell size, cell shape and nuclear to cytoplasmic ratio, nuclear detail, nuclear contour, prevalence of nucleoli, quality of cytoplasm and quantity of cytoplasm. In some embodiments, the immunofluorescent staining of nucleated cells comprises pan cytokeratin (CK), cluster of differentiation (CD) 45, and diamidino-2-phenylindole (DAPI). In some embodiments, the immunofluorescent staining of nucleated cells further comprises Androgen Receptor (AR).

In one aspect, the present invention describes a method for detecting progression of prostate cancer to CRPC in a patient comprising (a) performing a direct analysis comprising immunofluorescent staining and morphological characterization of nucleated cells in a blood sample obtained from the patient to detect circulating tumor cells (CTC); (b) determining prevalence of a CTC subpopulation associated with CRPC comprising detecting a measurable feature of each biomarker in a panel of morphological and protein biomarkers, wherein the presence of the CTC subpopulation associated with CRPC is indicative of CRPC, and (c) repeating steps (a) and (b), wherein an increase in the prevalence of the CTC population associated with CRPC indicates progression of prostate cancer to CRPC.

In some embodiments, the CRPC is metastatic castration-resistant prostate cancer (mCRPC). In some embodiments, the patient is undergoing hormone treatment. In some embodiments, the hormone treatment is androgen deprivation therapy (ADT). In some embodiments, the increased prevalence of a CTC subpopulation associated with CRPC comprises CK− CTCs. In other embodiments, the increased prevalence of a CTC subpopulation associated with CRPC comprises small CTCs. In some embodiments, the increase in the prevalence of the CTC population associated with CRPC predicts resistance to androgen deprivation therapy (ADT). In other embodiments, the increase in the prevalence the CTC population associated with mCRPC informs a subsequent decision to initiate secondary hormonal therapy directed at AR inhibition.

In some embodiments, the CRPC is mCRPC. In some embodiments, the patient is undergoing hormone treatment. In some embodiments, the increase in the prevalence of the CTC population associated with CRPC predicts resistance to hormone treatment. In some embodiments, the emerging CTC subpopulation associated with CRPC comprises CK− CTCs. In some embodiments, the emerging CTC subpopulation associated with CRPC comprises small CTCs. In some embodiments, the increase in the prevalence the CTC population associated with CRPC informs a subsequent decision to discontinue hormone treatment and/or initiate cytotoxic chemotherapy.

As described further below, CTCs, which are molecularly similar to metastatic biopsies, can be detected by high definition imaging of plated nucleated cells in blood samples from prostate cancer patients. Methods for detection and characterization of these CTCs based on a direct analysis comprising immunofluorescent staining and morphological characteristics of nucleated cells can be useful for earlier detection of mCRPC than presently available methods and can further inform the course of treatment of the patient based on phenotypic and/or molecular characterization of the CTCs.

It must be noted that, as used in this specification and the appended claims, the singular forms "a", "an" and "the" include plural referents unless the content clearly dictates otherwise. Thus, for example, reference to "a CTC" includes a mixture of two or more CTCs, and the like.

The term "about," particularly in reference to a given quantity, is meant to encompass deviations of plus or minus five percent.

As used in this application, including the appended claims, the singular forms "a," "an," and "the" include plural references, unless the content clearly dictates otherwise, and are used interchangeably with "at least one" and "one or more."

As used herein, the terms "comprises," "comprising," "includes," "including," "contains," "containing," and any variations thereof, are intended to cover a non-exclusive inclusion, such that a process, method, product-by-process, or composition of matter that comprises, includes, or contains an element or list of elements does not include only those elements but can include other elements not expressly listed or inherent to such process, method, product-by-process, or composition of matter.

The term "patient," as used herein preferably refers to a human, but also encompasses other mammals. It is noted that, as used herein, the terms "organism," "individual," "subject," or "patient" are used as synonyms and interchangeably.

As used herein, the term "circulating tumor cell" or "CTC" is meant to encompass any rare cell that is present in a biological sample and that is related to prostate cancer. CTCs, which can be present as single cells or in clusters of CTCs, are often epithelial cells shed from solid tumors found in very low concentrations in the circulation of patients. CTCs include "traditional CTCs," which are cytokeratin positive (CK+), CD45 negative (CD−), contain a DAPI nucleus, and are morphologically distinct from surrounding white blood cells. The term also encompasses "non-traditional CTCs" which differ from a traditional CTC in at least one characteristic. Non-traditional CTCs include the five CTC subpopulations, including CTC clusters, CK negative (CK$^-$) CTCs that are positive at least one additional biomarker that allows classification as a CTC, small CTCs, nucleoli$^+$ CTCs and CK speckled CTCs. As used herein, the term "CTC cluster" means two or more CTCs with touching cell membranes.

As used herein, a "subpopulation" refers to one or more CTCs that share morphological and/or immunofluorescent characteristics. As disclosed herein, CTC subpopulations associated with CRPC comprise CK− CTCs and/or small CTCs.

The majority of patients with systemic prostate cancer treated with androgen deprivation therapy (ADT), also referred to a "primary" hormone therapy in the context of prostate cancer, will develop castration-resistant prostate cancer (CRPC). Castration-resistant prostate cancer (CRCP) is defined by disease progression despite androgen deprivation therapy (ADT). CRPC can be categorized as nonmetastatic or metastatic (mCRPC). mCRPC refers to CRPC that has spread beyond the prostate gland to a distant site, such as lymph nodes or bone. The progression of CRCP can encompass as any combination of a rise in serum prostate-specific antigen (PSA), progression of pre-existing disease, and appearance of initial or new metastases. Most CRPCs select mechanisms that upregulate intracellular androgens and/or androgen receptor (AR), leading to ongoing AR-directed cancer growth despite a castrate level of serum androgens. Thus, when patients develop CRPC they are usually sensitive to sequential "secondary" hormonal therapies (antiandrogens, ketoconazole, estrogens) directed at AR inhibition.

As used herein, the term "predetermined threshold value" of the prevalence of a CTC subpopulation associated with CRPC, refers to the prevalence of the CTC subpopulation associated with CRPC in: (a) one or more corresponding control/normal samples obtained from the same patient; (b) one or more control/normal samples obtained from normal, or healthy, subjects, e.g. from males who do not have prostate cancer; or (c) a corresponding reference standard used by those skilled in the art.

As used herein, the term "prevalence" in regards to a CTC subpopulation associated with CRPC in a test biological sample refers to the number of CTCs in the sample that belong to the CTC subpopulation.

As described herein, an increased prevalence of CK−CTCs is indicative of CRPC in a patient. As further described herein, an increased prevalence of small CTCs is indicative of CRPC in a patient. While both CK− and small CTCs are subpopulations of CTCs and encompassed in the term "CTC" as defined herein, it is the increase in the relative proportion of these subpopulations among all CTCs in a sample that is indicative of CRPC. In its broadest sense, a biological sample can be any sample that contains CTCs.

A sample can comprise a bodily fluid such as blood; the soluble fraction of a cell preparation, or an aliquot of media in which cells were grown; a chromosome, an organelle, or membrane isolated or extracted from a cell; genomic DNA, RNA, or cDNA in solution or bound to a substrate; a cell; a tissue; a tissue print; a fingerprint; cells; skin, and the like. A biological sample obtained from a subject can be any sample that contains nucleated cells and encompasses any material in which CTCs can be detected. A sample can be, for example, whole blood, plasma, saliva or other bodily fluid or tissue that contains cells.

In particular embodiments, the biological sample is a blood sample. As described herein, a sample can be whole blood, more preferably peripheral blood or a peripheral blood cell fraction. As will be appreciated by those skilled in the art, a blood sample can include any fraction or component of blood, without limitation, T-cells, monocytes, neutrophiles, erythrocytes, platelets and microvesicles such as exosomes and exosome-like vesicles. In the context of this disclosure, blood cells included in a blood sample encompass any nucleated cells and are not limited to components of whole blood. As such, blood cells include, for example, both white blood cells (WBCs) as well as rare cells, including CTCs.

The samples of this disclosure can each contain a plurality of cell populations and cell subpopulation that are distinguishable by methods well known in the art (e.g., FACS, immunohistochemistry). For example, a blood sample can contain populations of non-nucleated cells, such as erythrocytes (e.g., 4-5 million/µl) or platelets (150,000-400,000 cells/µl), and populations of nucleated cells such as WBCs (e.g., 4,500-10,000 cells/µl), CECs or CTCs (circulating tumor cells; e.g., 2-800 cells/µl). WBCs may contain cellular subpopulations of, e.g., neutrophils (2,500-8,000 cells/µl), lymphocytes (1,000-4,000 cells/µl), monocytes (100-700 cells/µl), eosinophils (50-500 cells/µl), basophils (25-100 cells/µl) and the like. The samples of this disclosure are non-enriched samples, i.e., they are not enriched for any specific population or subpopulation of nucleated cells. For example, non-enriched blood samples are not enriched for CTCs, WBC, B-cells, T-cells, NK-cells, monocytes, or the like.

In some embodiments, the sample is a biological sample, for example, a blood sample, obtained from a subject who has been diagnosed with prostate cancer based on tissue or liquid biopsy and/or surgery or clinical grounds. In some embodiments, the blood sample is obtained from a subject showing a clinical manifestation of prostate cancer advancing to CRPC, including without limitation, rising PSA levels prior to diagnosis, after initial surgery or radiation, or despite hormone therapy. In some embodiments, the sample is obtained from a subject who has been on hormone therapy or who has had a bilateral orchiectomy and whose testosterone levels have dropped to less than 50 ng/dl, and who shows evidence of disease progression in the form of rising PSA levels or bone or soft tissue metastases. In some cases, the sample is obtained from a subject who has been undergoing primary hormone therapies, which are the LHRH agonists, for example, leuprolide (Lupron) or goserelin (Zoladex). In other embodiments, the biological sample is obtained from a healthy subject or a subject deemed to be at high risk for prostate cancer and/or metastasis of existing prostate cancer based on art known clinically established criteria including, for example, age, race, family and history.

As used herein, the term "direct analysis" means that the CTCs are detected in the context of all surrounding nucleated cells present in the sample as opposed to after enrichment of the sample for CTCs prior to detection. In some embodiments, the methods comprise microscopy providing a field of view that includes both CTCs and at least 200 surrounding white blood cells (WBCs).

A fundamental aspect of the present disclosure is the unparalleled robustness of the disclosed methods with regard to the detection of CTCs. The rare event detection disclosed herein with regard to CTCs is based on a direct analysis, i.e. non-enriched, of a population that encompasses the identification of rare events in the context of the surrounding non-rare events. Identification of the rare events according to the disclosed methods inherently identifies the surrounding events as non-rare events. Taking into account the surrounding non-rare events and determining the averages for non-rare events, for example, average cell size of non-rare events, allows for calibration of the detection method by removing noise. The result is a robustness of the disclosed methods that cannot be achieved with methods that are not based on direct analysis, but that instead compare enriched populations with inherently distorted contextual comparisons of rare events. The robustness of the direct analysis methods disclosed herein enables characterization of CTCs, including subpopulations of CTCs described herein, that cannot be achieved with other, enrichment-dependent CTC detection methods and that enables the identification and analysis of morphological and protein biomarkers indicative of the presence of a CTC subpopulation associated with CRPC in the context of the claimed methods. Approaches that enrich CTCs based on epithelial expression or physical characteristics are likely to miss non-traditional CTCs. Enumeration and characterization of non-traditional CTCs in mCRPC and other cancers provides prognostic/predictive information beyond traditional CTCs.

As described herein, the methods disclosed herein enable detection of CRPC in a patient afflicted with prostate cancer and make it possible to distinguish between different patient groups in the resistance setting in order to tailor subsequent treatment more precisely and effectively. The methods of the invention further allow for resistance monitoring of a prostate cancer patients by enabling detection of an emergence of CRPC in a patient afflicted with prostate cancer. The rapid evolution of drug therapies in prostate cancer has vastly improved upon the use of docetaxel since its pivotal US Food and Drug Administration (FDA) approval in 2004 and has brought about a new era where progress has been made beyond the use of androgen deprivation therapy (ADT) with the addition of novel hormonal agents, immunotherapy, second-line chemotherapy as well as radiopharmaceuticals. The choice of sequencing currently relies on patient profiles, whether symptoms of metastatic disease exist or not. While survival outcomes are undeniably improved with the use of these therapies, disease will ultimately progress on each regimen.

Androgens in the form of testosterone or the more potent dihydrotestosterone (DHT) have been well-defined drivers of progression of prostate cancer and differentiation of the prostate gland. As such, the backbone of treatment for advanced prostate cancers was established decades ago when castration in the form of surgical orchiectomy achieved significant prostate tumor regression. Since then, substitution to chemical castration has been employed mostly due to patient preference. ADT has therefore become the standard systemic treatment for locally advanced or metastatic prostate cancer. While ADT is almost always effective in most patients, disease progression to castration resistance inevitably occurs. It is now increasingly recognized that the androgen receptor (AR) remains overexpressed despite seemingly castrate levels of testosterone, since alternative receptors may activate the AR or other target genes may help perpetuate the castrate-resistant phenotype, hence the term "castration-resistance" has become widely adopted in the literature. The enhanced understanding of the role of these androgens in stimulating the growth of prostate cancer has led to the development and approval of a newer generation anti-androgen hormonal therapy drugs such as Zytiga (arbiterone), which blocks androgen production, and Xtandi (enzalutamide), an androgen receptor (AR) inhibitor. As described herein, the methods of the invention enable detection of CRPC in a patient afflicted with prostate cancer and make it possible to tailor subsequent treatment more precisely and effectively. The methods of the invention further allow for resistance monitoring of a prostate cancer patients by enabling detection of an emergence of CRPC in a patient afflicted with prostate cancer.

In some aspects, the disclosure provides a method for detecting castration-resistant prostate cancer (CRPC) in a patient afflicted with prostate cancer comprising (a) performing a direct analysis comprising immunofluorescent staining and morphological characterization of nucleated cells in a blood sample obtained from the patient to detect circulating tumor cells (CTC), (b) determining prevalence of a CTC subpopulation associated with CRPC comprising detecting a measurable feature of each biomarker in a panel of morphological and protein biomarkers, (c) comparing the prevalence of said CTC subpopulation to a predetermined threshold value, wherein the prevalence of the CTC subpopulation associated with CRPC above said predetermined threshold value is indicative of CRPC, and (c) repeating steps (a) through (c), wherein an increase in the prevalence of the CTC population associated with CRPC indicates progression of prostate cancer to CRPC. In some embodiments, the subject is undergoing primary hormone treatment.

In other aspects, the disclosure provides a method for monitoring disease progression in a subject afflicted with prostate cancer comprising (a) performing a direct analysis comprising immunofluorescent staining and morphological characterization of nucleated cells in a blood sample obtained from the patient to detect circulating tumor cells (CTC), (b) determining prevalence of a CTC subpopulation associated with CRPC comprising detecting a measurable feature of each biomarker in a panel of morphological and protein biomarkers, (c) comparing the prevalence of said CTC subpopulation to a predetermined threshold value, wherein the prevalence of the CTC subpopulation associated with CRPC above said predetermined threshold value is indicative of CRPC, and (c) repeating steps (a) through (c), wherein an increase in the prevalence of the CTC population associated with CRPC indicates progression of prostate cancer to CRPC. In some embodiments, the subject is undergoing androgen deprivation therapy (ADT) also referred to as "primary" hormone therapy.

In related aspects, the disclosure provides a method for resistance monitoring in a subject afflicted with prostate cancer comprising (a) performing a direct analysis comprising immunofluorescent staining and morphological characterization of nucleated cells in a blood sample obtained from the patient to detect circulating tumor cells (CTC), (b) determining prevalence of a CTC subpopulation associated with CRPC comprising detecting a measurable feature of each biomarker in a panel of morphological and protein biomarkers, (c) comparing the prevalence of said CTC subpopulation to a predetermined threshold value, wherein the prevalence of the CTC subpopulation associated with CRPC above said predetermined threshold value is indicative of CRPC, and (c) repeating steps (a) through (c), wherein an increase in the prevalence of the CTC population associated with CRPC indicates resistance to primary ADT.

In some embodiments of the methods disclosed herein, the patient is undergoing hormone treatment. In certain embodiments, the hormone treatment is primary ADT. In additional embodiments, the increase in the prevalence of the CTC population associated with CRPC predicts resistance to primary ADT and informs a subsequent decision to initiate secondary hormone treatment and/or to initiate cytotoxic therapy. In some embodiments, the subsequent treatment decision is a first "secondary" hormone therapy, such as antiandrogens and ketoconazole, which are options for nonmetastatic CRPC. In other embodiments, the subsequent treatment decision is a second-generation antiandrogen such as Enzalutamide (Xtandi), which is more potent than first-generation antiandrogens because of its ability to block nuclear translocation of AR and approved for use in mCRPC, or abiraterone (Zytiga), which is a potent androgen synthesis inhibitor. In some embodiments, the subsequent treatment decision is cytotoxic chemotherapy with a platinum-based regimen, for example and without limitation, docetaxel (Taxotere®), mitoxantronepaclitaxel (Taxol®) and cabazitaxel.

In some embodiments, the methods for detecting CRPC in a patient afflicted with prostate cancer can further encompass individual patient risk factors, clinical, biopsy or imaging data, which includes any form of imaging modality known and used in the art, for example and without limitation, by X-ray computed tomography (CT), ultrasound, positron emission tomography (PET), electrical impedance tomography and magnetic resonance (MRI). It is understood that one skilled in the art can select an imaging modality based on a variety of art known criteria. Additionally, the methods disclosed herein, can optionally encompass one or more one or more individual risk factors that can be selected from the group consisting of, for example, age, race, family history, clinical history and/or data.

Risk factors for CRPC in the context of clinical data further include, for example, include PSA, bone turnover markers, bone pain, bone scans. In those cases, biopsies can be performed to confirm or rule out mCRPC and methods for detecting mCRPC in a patient afflicted with prostate cancer can further take encompass as a risk factor the resultant biopsy data. It is understood that one skilled in the art can select additional individual risk factors based on a variety of art known criteria. As described herein, the methods of the invention can encompass one or more individual risk factors. Accordingly, biomarkers can include, without limitation, imaging data, clinical data, biopsy data, and individual risk factors. As described herein, biomarkers also can include, but are not limited to, biological molecules comprising nucleotides, nucleic acids, nucleosides, amino acids, sugars, fatty acids, steroids, metabolites, peptides, polypeptides, proteins, carbohydrates, lipids, hormones, antibodies, regions of interest that serve as surrogates for biological macromolecules and combinations thereof (e.g., glycoproteins, ribonucleoproteins, lipoproteins) as well as portions or fragments of a biological molecule.

Direct analysis of CTCs according to the methods of the invention can include both morphological features and immunofluorescent features. As will be understood by those skilled in the art, biomarkers can include a biological molecule, or a fragment of a biological molecule, the change and/or the detection of which can be correlated, individually or combined with other measurable features, with mCRPC. CTCs, which can be present a single cells or in clusters of CTCs, are often epithelial cells shed from solid tumors and are present in very low concentrations in the circulation of subjects. Accordingly, detection of CTCs in a blood sample can be referred to as rare event detection. CTCs have an abundance of less than 1:1,000 in a blood cell population, e.g., an abundance of less than 1:5,000, 1:10,000, 1:30,000, 1:50:000, 1:100,000, 1:300,000, 1:500,000, or 1:1,000,000. In some embodiments, the a CTC has an abundance of 1:50:000 to 1:100,000 in the cell population.

The samples of this disclosure may be obtained by any means, including, e.g., by means of solid tissue biopsy or fluid biopsy (see, e.g., Marrinucci D. et al., 2012, Phys. Biol. 9 016003). Briefly, in particular embodiments, the process can encompass lysis and removal of the red blood cells in a 7.5 mL blood sample, deposition of the remaining nucleated cells on specialized microscope slides, each of which accommodates the equivalent of roughly 0.5 mL of whole blood. A blood sample may be extracted from any source known to include blood cells or components thereof, such as venous, arterial, peripheral, tissue, cord, and the like. The samples may be processed using well known and routine clinical methods (e.g., procedures for drawing and processing whole blood). In some embodiments, a blood sample is drawn into anti-coagulent blood collection tubes (BCT), which may contain EDTA or Streck Cell-Free DNA™. In other embodiments, a blood sample is drawn into CellSave® tubes (Veridex). A blood sample may further be stored for up to 12 hours, 24 hours, 36 hours, 48 hours, or 60 hours before further processing.

In some embodiments, the methods of this disclosure comprise an initial step of obtaining a white blood cell (WBC) count for the blood sample. In certain embodiments, the WBC count may be obtained by using a HemoCue® WBC device (Hemocue, Ängelholm, Sweden). In some embodiments, the WBC count is used to determine the amount of blood required to plate a consistent loading volume of nucleated cells per slide and to calculate back the equivalent of CTCs per blood volume.

In some embodiments, the methods of this disclosure comprise an initial step of lysing erythrocytes in the blood sample. In some embodiments, the erythrocytes are lysed, e.g., by adding an ammonium chloride solution to the blood sample. In certain embodiments, a blood sample is subjected to centrifugation following erythrocyte lysis and nucleated cells are resuspended, e.g., in a PBS solution.

In some embodiments, nucleated cells from a sample, such as a blood sample, are deposited as a monolayer on a planar support. The planar support may be of any material, e.g., any fluorescently clear material, any material conducive to cell attachment, any material conducive to the easy removal of cell debris, any material having a thickness of <100 μm. In some embodiments, the material is a film. In some embodiments the material is a glass slide. In certain embodiments, the method encompasses an initial step of depositing nucleated cells from the blood sample as a monolayer on a glass slide. The glass slide can be coated to allow maximal retention of live cells (See, e.g., Marrinucci D. et al., 2012, Phys. Biol. 9 016003). In some embodiments, about 0.5 million, 1 million, 1.5 million, 2 million, 2.5 million, 3 million, 3.5 million, 4 million, 4.5 million, or 5 million nucleated cells are deposited onto the glass slide. In some embodiments, the methods of this disclosure comprise depositing about 3 million cells onto a glass slide. In additional embodiments, the methods of this disclosure comprise depositing between about 2 million and about 3 million cells onto the glass slide. In some embodiments, the glass slide and immobilized cellular samples are available for further processing or experimentation after the methods of this disclosure have been completed.

In some embodiments, the methods of this disclosure comprise an initial step of identifying nucleated cells in the non-enriched blood sample. In some embodiments, the nucleated cells are identified with a fluorescent stain. In certain embodiments, the fluorescent stain comprises a nucleic acid specific stain. In certain embodiments, the fluorescent stain is diamidino-2-phenylindole (DAPI). In some embodiments, immunofluorescent staining of nucleated cells comprises pan cytokeratin (CK), cluster of differentiation (CD) 45 and DAPI. In some embodiments further described herein, CTCs comprise distinct immunofluorescent staining from surrounding nucleated cells. In some embodiments, the distinct immunofluorescent staining of CTCs comprises DAPI (+), CK (+) and CD 45 (−). In some embodiments, the identification of CTCs further comprises comparing the intensity of pan cytokeratin fluorescent staining to surrounding nucleated cells. In some embodiments, the CTCs are CK− CTCs, that are identified as CTC based on other characteristics. As described herein, CTCs detected in the methods of the invention encompass traditional CTCs, cytokeratin negative (CK⁻) CTCs, small CTCs, and CTC clusters. In some embodiments, the CTC detection and analysis is accomplished by fluorescent scanning microscopy to detect immunofluorescent staining of nucleated cells in a blood sample. Marrinucci D. et al., 2012, Phys. Biol. 9 016003).

In particular embodiments, all nucleated cells are retained and immunofluorescently stained with monoclonal antibodies targeting cytokeratin (CK), an intermediate filament found exclusively in epithelial cells, a pan leukocyte specific antibody targeting the common leukocyte antigen CD45, and a nuclear stain, DAPI. The nucleated blood cells can be imaged in multiple fluorescent channels to produce high quality and high resolution digital images that retain fine cytologic details of nuclear contour and cytoplasmic distribution. While the surrounding WBCs can be identified with the pan leukocyte specific antibody targeting CD45, traditional CTCs can be identified, for example, as DAPI (+), CK (+) and CD 45 (−). In the methods described herein, the CTCs comprise distinct immunofluorescent staining from surrounding nucleated cells.

As described herein, CTCs encompass traditional CTCs, also referred to as high definition CTCs (HD-CTCs). Traditional CTCs are CK positive, CD45 negative, contain an intact DAPI positive nucleus without identifiable apoptotic changes or a disrupted appearance, and are morphologically distinct from surrounding white blood cells (WBCs). DAPI (+), CK (+) and CD45 (−) intensities can be categorized as measurable features during CTC enumeration as previously described. Nieva et al., Phys Biol 9:016004 (2012). The enrichment-free, direct analysis employed by the methods disclosed herein results in high sensitivity and high specificity, while adding high definition cytomorphology to enable detailed morphologic characterization of a CTC population known to be heterogeneous. In some embodiments, the morphological characteristics of a CTC detected in the methods of the invention comprise one or more of the group consisting of nucleus size, nucleus shape, presence of holes in nucleus, cell size, cell shape and nuclear to cytoplasmic ratio, nuclear detail, nuclear contour, prevalence of nucleoli, quality of cytoplasm and quantity of cytoplasm.

As described herein, the methods for detecting CRPC in a patient afflicted with prostate cancer encompass determining the prevalence of a CTC subpopulation associated with CRPC comprising detecting a measurable feature of a panel of morphological and protein biomarkers, wherein the increased presence of the CTC subpopulation associated with CRPC is indicative of mCRPC. In particular embodiments, the protein biomarkers in step (b) comprise the Androgen Receptor (AR) and pan cytokeratin (CK). In additional embodiments, the morphological biomarkers unique to the CTC subpopulation associated with mCRPC comprise small size. In additional embodiments, determining the presence of a CTC subpopulation associated with CRPC comprises analysis of the CTCs at the single cell level.

While traditional CTCs can be immunofluorescently identified as comprising DAPI (+), CK (+) and CD 45 (−) cells, the methods of the invention can be practiced with any other biomarkers that one of skill in the art selects for detecting traditional and non-traditional CTCs in a biological sample. One skilled in the art knows how to select a morphological feature, biological molecule, or a fragment of a biological molecule, the change and/or the detection of which can be correlated with a CTC. Molecule biomarkers include, but are not limited to, biological molecules comprising nucleotides, nucleic acids, nucleosides, amino acids, sugars, fatty acids, steroids, metabolites, peptides, polypeptides, proteins, carbohydrates, lipids, hormones, antibodies, regions of interest that serve as surrogates for biological macromolecules and combinations thereof (e.g., glycoproteins, ribonucleoproteins, lipoproteins). The term also encompasses portions or fragments of a biological molecule, for example, peptide fragment of a protein or polypeptide.

A person skilled in the art will appreciate that a number of methods can be used to detect and analyze CTCs, including microscopy based approaches, including fluorescence scanning microscopy (see, e.g., Marrinucci D. et al., 2012, Phys. Biol. 9 016003), mass spectrometry approaches, such as MS/MS, LC-MS/MS, multiple reaction monitoring (MRM) or SRM and product-ion monitoring (PIM) and also including antibody based methods such as immunofluorescence, immunohistochemistry, immunoassays such as Western blots, enzyme-linked immunosorbant assay (ELISA), immunopercipitation, radioimmunoassay, dot blotting, and FACS. Immunoassay techniques and protocols are generally known to those skilled in the art (Price and Newman, *Principles and Practice of Immunoassay*, 2nd Edition, Grove's Dictionaries, 1997; and Gosling, *Immunoassays: A Practical Approach*, Oxford University Press, 2000.) A variety of immunoassay techniques, including competitive and non-competitive immunoassays, can be used (Self et al., *Curr. Opin. Biotechnol.*, 7:60-65 (1996), see also John R. Crowther, *The ELISA Guidebook*, 1st ed., Humana Press 2000, ISBN 0896037282 and, *An Introduction to Radioimmunoassay and Related Techniques*, by Chard T, ed., Elsevier Science 1995, ISBN 0444821198).

A person of skill in the art will further appreciate that the prevalence of protein biomarkers may be detected using any class of marker-specific binding reagents known in the art, including, e.g., antibodies, aptamers, fusion proteins, such as fusion proteins including protein receptor or protein ligand components, or biomarker-specific small molecule binders. In some embodiments, the prevalence of AR, CK or CD45 is determined by an antibody.

The antibodies of this disclosure bind specifically to a protein biomarker. The antibody can be prepared using any suitable methods known in the art. See, e.g., Coligan, *Current Protocols in Immunology* (1991); Harlow & Lane, *Antibodies: A Laboratory Manual* (1988); Goding, *Monoclonal Antibodies: Principles and Practice* (2d ed. 1986). The antibody can be any immunoglobulin or derivative thereof, whether natural or wholly or partially synthetically produced. All derivatives thereof which maintain specific binding ability are also included in the term. The antibody has a binding domain that is homologous or largely homologous to an immunoglobulin binding domain and can be derived from natural sources, or partly or wholly synthetically produced. The antibody can be a monoclonal or polyclonal antibody. In some embodiments, an antibody is a single chain antibody. Those of ordinary skill in the art will appreciate that antibody can be provided in any of a variety of forms including, for example, humanized, partially humanized, chimeric, chimeric humanized, etc. The antibody can be an antibody fragment including, but not limited to, Fab, Fab', F(ab')2, scFv, Fv, dsFv diabody, and Fd fragments. The antibody can be produced by any means. For example, the antibody can be enzymatically or chemically produced by fragmentation of an intact antibody and/or it can be recombinantly produced from a gene encoding the partial antibody sequence. The antibody can comprise a single chain antibody fragment. Alternatively or additionally, the antibody can comprise multiple chains which are linked together, for example, by disulfide linkages, and any functional fragments obtained from such molecules, wherein such fragments retain specific-binding properties of the parent antibody molecule. Because of their smaller size as functional components of the whole molecule, antibody fragments can offer advantages over intact antibodies for use in certain immunochemical techniques and experimental applications.

A detectable label can be used in the methods described herein for direct or indirect detection of the biomarkers when practicing the methods of the invention. A wide variety of detectable labels can be used, with the choice of label depending on the sensitivity required, ease of conjugation with the antibody, stability requirements, and available instrumentation and disposal provisions. Those skilled in the art are familiar with selection of a suitable detectable label based on the assay detection of the biomarkers in the methods of the invention. Suitable detectable labels include, but are not limited to, fluorescent dyes (e.g., fluorescein, fluorescein isothiocyanate (FITC), Oregon Green™, rhodamine, Texas red, tetrarhodimine isothiocynate (TRITC), Cy3, Cy5, Alexa Fluor® 647, Alexa Fluor® 555, Alexa Fluor® 488), fluorescent markers (e.g., green fluorescent protein (GFP), phycoerythrin, etc.), enzymes (e.g., luciferase, horseradish peroxidase, alkaline phosphatase, etc.), nanoparticles, biotin, digoxigenin, metals, and the like.

For mass-sectrometry based analysis, differential tagging with isotopic reagents, e.g., isotope-coded affinity tags (ICAT) or the more recent variation that uses isobaric tagging reagents, iTRAQ (Applied Biosystems, Foster City, Calif.), followed by multidimensional liquid chromatography (LC) and tandem mass spectrometry (MS/MS) analysis can provide a further methodology in practicing the methods of this disclosure.

A chemiluminescence assay using a chemiluminescent antibody can be used for sensitive, non-radioactive detection of proteins. An antibody labeled with fluorochrome also can be suitable. Examples of fluorochromes include, without limitation, DAPI, fluorescein, Hoechst 33258, R-phycocyanin, B-phycoerythrin, R-phycoerythrin, rhodamine, Texas red, and lissamine. Indirect labels include various enzymes well known in the art, such as horseradish peroxidase (HRP), alkaline phosphatase (AP), beta-galactosidase, urease, and the like. Detection systems using suitable substrates for horseradish-peroxidase, alkaline phosphatase, beta.-galactosidase are well known in the art.

A signal from the direct or indirect label can be analyzed, for example, using a microscope, such as a fluorescence microscope or a fluorescence scanning microscope. Alternatively, a spectrophotometer can be used to detect color from a chromogenic substrate; a radiation counter to detect radiation such as a gamma counter for detection of $^{125}$I; or a fluorometer to detect fluorescence in the presence of light of a certain wavelength. If desired, assays used to practice the methods of this disclosure can be automated or performed robotically, and the signal from multiple samples can be detected simultaneously.

In some embodiments, the biomarkers are immunofluorescent markers. In some embodiments, the immunofluorescent makers comprise a marker specific for epithelial cells. In some embodiments, the immunofluorescent makers comprise a marker specific for white blood cells (WBCs). In some embodiments, one or more of the immunofluorescent markers comprise CD45 and CK.

In some embodiments, the prevalence of immunofluorescent markers in nucleated cells, such as CTCs or WBCs, results in distinct immunofluorescent staining patterns. Immunofluorescent staining patterns for CTCs and WBCs may differ based on which epithelial or WBC markers are detected in the respective cells. In some embodiments, determining prevalence of one or more immunofluorescent markers comprises comparing the distinct immunofluorescent staining of CTCs with the distinct immunofluorescent staining of WBCs using, for example, immunofluorescent staining of CD45, which distinctly identifies WBCs. There are other detectable markers or combinations of detectable markers that bind to the various subpopulations of WBCs. These may be used in various combinations, including in combination with or as an alternative to immunofluorescent staining of CD45.

In some embodiments, CTCs comprise distinct morphological characteristics compared to surrounding nucleated cells. In some embodiments, the morphological characteristics comprise nucleus size, nucleus shape, cell size, cell shape, and/or nuclear to cytoplasmic ratio. In some embodiments, the method further comprises analyzing the nucleated cells by nuclear detail, nuclear contour, prevalence of nucleoli, quality of cytoplasm, quantity of cytoplasm, intensity of immunofluorescent staining patterns. A person of ordinary skill in the art understands that the morphological characteristics of this disclosure may include any feature, property, characteristic, or aspect of a cell that can be determined and correlated with the detection of a CTC. In particular embodiments, the morphological characteristics analyzed in the methods of the invention comprise one or more of the group consisting of nucleus size, nucleus shape, presence of holes in nucleus, cell size, cell shape and nuclear to cytoplasmic ratio, nuclear detail, nuclear contour, prevalence of nucleoli, quality of cytoplasm and quantity of cytoplasm.

Detection and analysis of CTCs can be performed with any suitable microscopic method known in the art. In some embodiments, the method is performed by fluorescent scanning microscopy. In certain embodiments the microscopic method provides high-resolution images of CTCs and their surrounding WBCs (see, e.g., Marrinucci D. et al., 2012, Phys. Biol. 9 016003)). In some embodiments, a slide coated with a monolayer of nucleated cells from a sample, such as a non-enriched blood sample, is scanned by a fluorescent scanning microscope and the fluorescence intensities from immunofluorescent markers and nuclear stains are recorded to allow for the determination of the prevalence of each immunofluorescent marker and the assessment of the morphology of the nucleated cells. In some embodiments, microscopic data collection and analysis is conducted in an automated manner.

In some embodiments, the methods of the invention include detecting one or more biomarkers, for example, AR, CK and CD 45. A biomarker is considered present in a cell if it is detectable above the background noise of the respective detection method used (e.g., 2-fold, 3-fold, 5-fold, or 10-fold higher than the background; e.g., 2σ or 3σ over background). In some embodiments, a biomarker is considered absent if it is not detectable above the background noise of the detection method used (e.g., <1.5-fold or <2.0-fold higher than the background signal; e.g., <1.5σ or <2.0σ over background).

In some embodiments, the prevalence of immunofluorescent markers in nucleated cells is determined by selecting the exposure times during the fluorescence scanning process such that all immunofluorescent markers achieve a pre-set level of fluorescence on the WBCs in the field of view. Under these conditions, CTC-specific immunofluorescent markers, even though absent on WBCs are visible in the WBCs as background signals with fixed heights. Moreover, WBC-specific immunofluorescent markers that are absent on CTCs are visible in the CTCs as background signals with fixed heights. A cell is considered positive for an immunofluorescent marker (i.e., the marker is considered present) if its fluorescent signal for the respective marker is significantly higher than the fixed background signal (e.g., 2-fold, 3-fold, 5-fold, or 10-fold higher than the background; e.g., 2σ or 3σ over background). For example, a nucleated cell is considered CD 45 positive (CD 45$^+$) if its fluorescent signal for CD 45 is significantly higher than the background signal. A cell is considered negative for an immunofluorescent marker (i.e., the marker is considered absent) if the cell's fluorescence signal for the respective marker is not significantly above the background signal (e.g., <1.5-fold or <2.0-fold higher than the background signal; e.g., <1.5σ or <2.0σ over background).

Typically, each microscopic field contains both CTCs and WBCs. In certain embodiments, the microscopic field shows at least 1, 5, 10, 20, 50, or 100 CTCs. In certain embodiments, the microscopic field shows at least 10, 25, 50, 100, 250, 500, or 1,000 fold more WBCs than CTCs. In certain embodiments, the microscopic field comprises one or more CTCs or CTC clusters surrounded by at least 10, 50, 100, 150, 200, 250, 500, 1,000 or more WBCs.

In some embodiments of the methods described herein, detection of CTCs comprises enumeration of CTCs that are present in the blood sample. In some embodiments, the methods described herein encompass detection of at least 1.0 CTC/mL of blood, 1.5 CTCs/mL of blood, 2.0 CTCs/mL of blood, 2.5 CTCs/mL of blood, 3.0 CTCs/mL of blood, 3.5 CTCs/mL of blood, 4.0 CTCs/mL of blood, 4.5 CTCs/mL of blood, 5.0 CTCs/mL of blood, 5.5 CTCs/mL of blood, 6.0 CTCs/mL of blood, 6.5 CTCs/mL of blood, 7.0 CTCs/mL of blood, 7.5 CTCs/mL of blood, 8.0 CTCs/mL of blood, 8.5 CTCs/mL of blood, 9.0 CTCs/mL of blood, 9.5 CTCs/mL of blood, 10 CTCs/mL of blood, or more.

In some embodiments of methods described herein, the CTCs detected in a biological sample comprise distinct subtypes of CTCs, including non-traditional CTCs. In some embodiments, the methods described herein encompass detection of at least 0.1 CTC cluster/mL of blood, 0.2 CTC clusters/mL of blood, 0.3 CTC clusters/mL of blood, 0.4 CTC clusters/mL of blood, 0.5 CTC clusters/mL of blood, 0.6 CTC clusters/mL of blood, 0.7 CTC clusters/mL of blood, 0.8 CTC clusters/mL of blood, 0.9 CTC clusters/mL of blood, 1 CTC cluster/mL of blood, 2 CTC clusters/mL of blood, 3 CTC clusters/mL of blood, 4 CTC clusters/mL of blood, 5 CTC clusters/mL of blood, 6 CTC clusters/mL of blood, 7 CTC clusters/mL of blood, 8 CTC clusters/mL of blood, 9 CTC clusters/mL of blood, 10 clusters/mL or more. In a particular embodiment, the methods described herein encompass detection of at least 1 CTC cluster/mL of blood In some embodiments, the methods for detecting CRPC in a patient afflicted with prostate cancer comprising molecular analysis of the CTCs further comprise molecular characterization of the CTCs, for example, by fluorescence in situ hybridization (FISH). In additional embodiments, the FISH analysis detects rearrangement of erythroblast transformation-specific (ETS)-related gene (ERG). In further embodiments, the FISH analysis detects loss of Phosphatase and tensin homolog gene (PTEN).

Standard molecular biology techniques known in the art and not specifically described are generally followed as in Sambrook et al., Molecular Cloning: A Laboratory Manual, Cold Spring Harbor Laboratory Press, New York (1989), and as in Ausubel et al., Current Protocols in Molecular Biology, John Wiley and Sons, Baltimore, Md. (1989) and as in Perbal, A Practical Guide to Molecular Cloning, John Wiley & Sons, New York (1988), and as in Watson et al., Recombinant DNA, Scientific American Books, New York and in Birren et al (eds) Genome Analysis: A Laboratory Manual Series, Vols. 1-4 Cold Spring Harbor Laboratory Press, New York (1998). Polymerase chain reaction (PCR) can be carried out generally as in PCR Protocols: A Guide to Methods and Applications, Academic Press, San Diego, Calif. (1990). Any method capable of determining a DNA copy number profile of a particular sample can be used for molecular profiling according to the invention provided the resolution is sufficient to identify the biomarkers of the invention. The skilled artisan is aware of and capable of using a number of different platforms for assessing whole genome copy number changes at a resolution sufficient to identify the copy number of the one or more biomarkers of the invention.

In situ hybridization assays are well known and are generally described in Angerer et al., Methods Enzymol. 152:649-660 (1987). In an in situ hybridization assay, cells, e.g., from a biopsy, are fixed to a solid support, typically a glass slide. If DNA is to be probed, the cells are denatured with heat or alkali. The cells are then contacted with a hybridization solution at a moderate temperature to permit annealing of specific probes that are labeled. The probes are preferably labeled with radioisotopes or fluorescent reporters. FISH (fluorescence in situ hybridization) uses fluorescent probes that bind to only those parts of a sequence with which they show a high degree of sequence similarity.

FISH is a cytogenetic technique used to detect and localize specific polynucleotide sequences in cells. For example, FISH can be used to detect DNA sequences on chromosomes. FISH can also be used to detect and localize specific RNAs, e.g., mRNAs, within tissue samples. In FISH uses fluorescent probes that bind to specific nucleotide sequences to which they show a high degree of sequence similarity. Fluorescence microscopy can be used to find out whether and where the fluorescent probes are bound. In addition to detecting specific nucleotide sequences, e.g., translocations, fusion, breaks, duplications and other chromosomal abnormalities, FISH can help define the spatial-temporal patterns of specific gene copy number and/or gene expression within cells and tissues.

In some embodiments, the disclosed methods for detecting CRPC in a patient afflicted with prostate cancer encompass the use of a predictive model. In further embodiments, the disclosed methods method for detecting CRPC in a patient afflicted with prostate cancer encompass comparing a measurable feature with a reference feature. As those skilled in the art can appreciate, such comparison can be a direct comparison to the reference feature or an indirect comparison where the reference feature has been incorporated into the predictive model. In further embodiments, analyzing a measurable feature in a method for detecting CRPC in a patient afflicted with prostate cancer encompasses one or more of a linear discriminant analysis model, a support vector machine classification algorithm, a recursive feature elimination model, a prediction analysis of microarray model, a logistic regression model, a CART algorithm, a flex tree algorithm, a LART algorithm, a random forest algorithm, a MART algorithm, a machine learning algorithm, a penalized regression method, or a combination thereof. In particular embodiments, the analysis comprises logistic regression. In additional embodiments, the detection of mCRPC in a patient afflicted with prostate cancer is expressed as a risk score.

An analytic classification process can use any one of a variety of statistical analytic methods to manipulate the quantitative data and provide for classification of the sample. Examples of useful methods include linear discriminant analysis, recursive feature elimination, a prediction analysis of microarray, a logistic regression, a CART algorithm, a FlexTree algorithm, a LART algorithm, a random forest algorithm, a MART algorithm, machine learning algorithms and other methods known to those skilled in the art.

Classification can be made according to predictive modeling methods that set a threshold for determining the probability that a sample belongs to a given class. The probability preferably is at least 50%, or at least 60%, or at least 70%, or at least 80%, or at least 90% or higher. Classifications also can be made by determining whether a comparison between an obtained dataset and a reference dataset yields a statistically significant difference. If so, then the sample from which the dataset was obtained is classified as not belonging to the reference dataset class. Conversely, if such a comparison is not statistically significantly different from the reference dataset, then the sample from which the dataset was obtained is classified as belonging to the reference dataset class.

The predictive ability of a model can be evaluated according to its ability to provide a quality metric, e.g. AUROC (area under the ROC curve) or accuracy, of a particular value, or range of values. Area under the curve measures are useful for comparing the accuracy of a classifier across the complete data range. Classifiers with a greater AUC have a greater capacity to classify unknowns correctly between two groups of interest. ROC analysis can be used to select the optimal threshold under a variety of clinical circumstances, balancing the inherent tradeoffs that exist between specificity and sensitivity. In some embodiments, a desired quality threshold is a predictive model that will classify a sample with an accuracy of at least about 0.7, at least about 0.75, at least about 0.8, at least about 0.85, at least about 0.9, at least about 0.95, or higher. As an alternative measure, a desired quality threshold can refer to a predictive model that will classify a sample with an AUC of at least about 0.7, at least about 0.75, at least about 0.8, at least about 0.85, at least about 0.9, or higher.

As is known in the art, the relative sensitivity and specificity of a predictive model can be adjusted to favor either the specificity metric or the sensitivity metric, where the two metrics have an inverse relationship. The limits in a model as described above can be adjusted to provide a selected sensitivity or specificity level, depending on the particular requirements of the test being performed. One or both of sensitivity and specificity can be at least about 0.7, at least about 0.75, at least about 0.8, at least about 0.85, at least about 0.9, or higher.

The raw data can be initially analyzed by measuring the values for each measurable feature or biomarker, usually in triplicate or in multiple triplicates. The data can be manipulated, for example, raw data can be transformed using standard curves, and the average of triplicate measurements used to calculate the average and standard deviation for each patient. These values can be transformed before being used in the models, e.g. log-transformed, Box-Cox transformed (Box and Cox, *Royal Stat. Soc.*, Series B, 26:211-246 (1964). The data are then input into a predictive model, which will classify the sample according to the state. The resulting information can be communicated to a patient or health care provider.

In some embodiments, the method disclosed herein for detecting CRPC in a patient afflicted with prostate cancer has a specificity of >60%, >70%, >80%, >90% or higher. In additional embodiments, the method disclosed herein for detecting CRPC in a patient afflicted with prostate cancer has a specificity>90% at a classification threshold of 7.5 CTCs/mL of blood.

From the foregoing description, it will be apparent that variations and modifications can be made to the invention described herein to adopt it to various usages and conditions. Such embodiments are also within the scope of the following claims.

The recitation of a listing of elements in any definition of a variable herein includes definitions of that variable as any single element or combination (or subcombination) of listed elements. The recitation of an embodiment herein includes that embodiment as any single embodiment or in combination with any other embodiments or portions thereof.

All patents and publications mentioned in this specification are herein incorporated by reference to the same extent as if each independent patent and publication was specifically and individually indicated to be incorporated by reference.

The following examples are provided by way of illustration, not limitation.

EXAMPLES

Example 1. Identification of CTC Subpopulation Indicative of CRPC

Blood from 10 healthy volunteers (HV) and 39 mCRPC patients (pts) was collected and shipped to Epic Sciences, where all nucleated cells were plated onto glass slides and subjected to immunofluorescence (IF) staining and CTC identification by fluorescent scanners and algorithms. Traditional CTCs were identified as CK+CD45− cells with intact DAPI nuclei and after pathologist review of their morphology. Candidate CK− CTC populations were defined as CK−CD45− that were morphologically malignant. Small nuclear size candidate CTCs were identified as CK+CD45− cells with diameters similar to or smaller than that of a typical white blood cells (WBCs). All candidate CTCs were evaluated with prostate cancer relevant biomarkers, including androgen receptor (AR) IF and PTEN loss and ERG rearrangements by FISH.

Cells were identified as follows: CD45− cells with an intact nucleus (i.e., exclude apoptotic) plus one or a combination of the following characteristics: abnormal cancer-like morphology and/or positive for a positive for cancer-specific biomarker. Cluster-like morphology (i.e., a cell cluster) and cancer genomics were also used as confirmation after morphological and/or protein biomarker detection.

Results: 38/39 patients had 1 or more traditional CTCs/mL and 36/39 pts had 1 or more CK− CTCs/mL of blood. 8/39 samples had >10 CK− CTCs/mL. 15/39 samples had evidence of small nuclear size CTCs at varying incidences and sizes of cells. We observed PCa biomarkers including high AR expression, PTEN deletion, and ERG rearrangements in both CK− and small nuclear size CTCs. These features were not observed in over 1,000 WBCs evaluated and healthy volunteers.

Example 2. Further Studies of CTC Subpopulations Indicative of CRPC

This example describes additional studies of CTC subpopulations indicative of CRPC.

CTCs are traditionally defined as EpCAM/CK+ cells, CD45−, and morphologically distinct. However, recent evidence suggests that other populations of CTC candidates exist, including cells that are EpCAM/CK− or smaller in size than traditional CTCs. CTC positive selection techniques that isolate CTCs based on size, density or EpCAM positivity may miss CTC subpopulations. These studies were aimed at molecularly characterizing novel CTC candidates utilizing a platform that involves no physical selection.

Figure 1A:
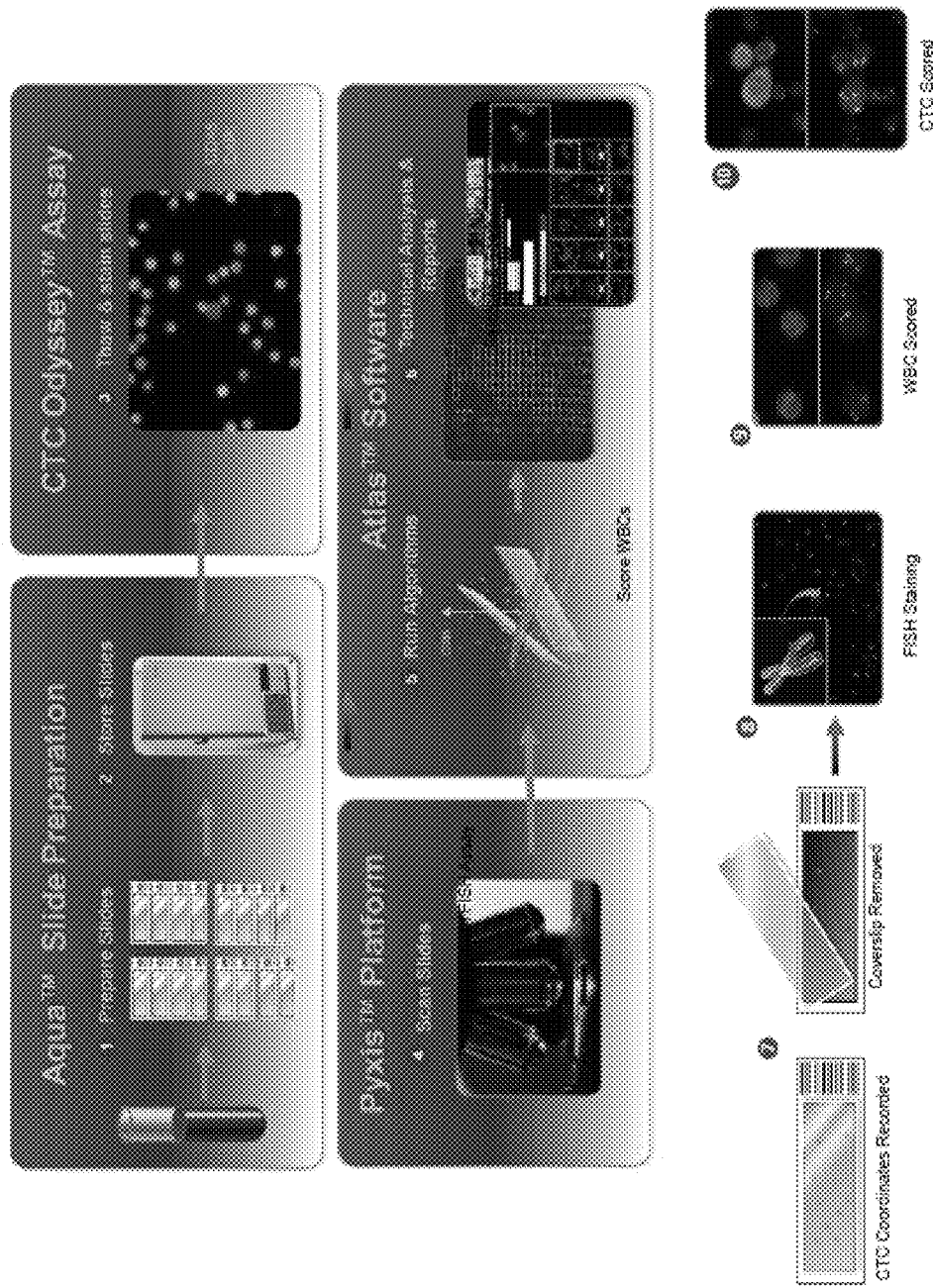

Blood from 10 healthy volunteers (HV) and 41 patients (pts) with metastatic castration-resistant prostate cancer (mCRPC) were collected and shipped to Epic Sciences, where cells were identified utilizing an Epic CTC collection and detection process (see FIG. 1A). Traditional CTCs were identified as CK+CD45− cells with intact DAPI nuclei and after pathologist review of their morphology. Candidate CK− CTC populations were identified as CK−CD45− that were morphologically malignant. Small nuclear size candidate CTCs were identified as CK+CD45− cells with diameters similar to or smaller than that of adjacent white blood cells (WBCs). Candidate CTC were evaluated with prostate cancer relevant biomarkers, including androgen receptor (AR) expression, by immunofluorescence (IF) and PTEN loss and ERG rearrangements by FISH. Lab personnel were blinded to the clinical data. Characteristics of the study population are provided in FIG. 1B.

Figure 2C:
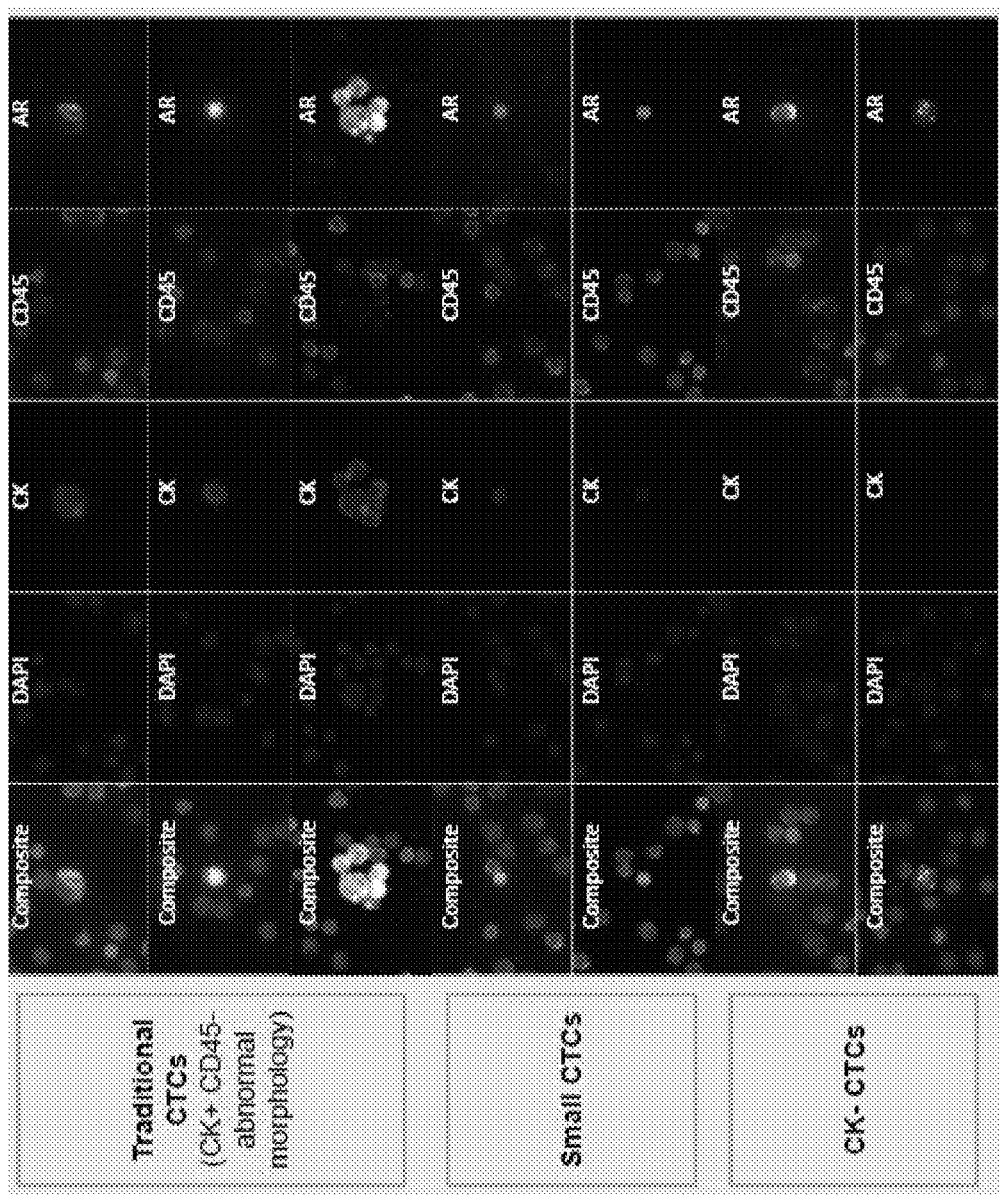

Traditional CTCs were detected in 39 of 41 patients, with a median of 5 CTCs/mL of blood (see FIG. 2A). Other CTC populations (e.g., CK− cells, apoptotic cells, small nuclear size cells) were identified in all of the samples analyzed. Overall, a positive correlation between traditional CTC count and other CTC population count was found: CK− (Spearman's correlation coefficient, r=0.45, P=0.003), small nuclear size (r=0.50, P=0.0007), and apoptotic cells (r=0.68, P<0.001). Patients with visceral disease had higher small cells count than patients with bone and nodal disease only (median 0.5/mL vs 2/mL; p=0.0 Mann-Whitney test). AR expression studies are shown in FIG. 2B. As shown in FIG. 2C, CK− CTCs and small CTCs with cancer related morphology and expression of AR proteins were identified.

Figure 3A:
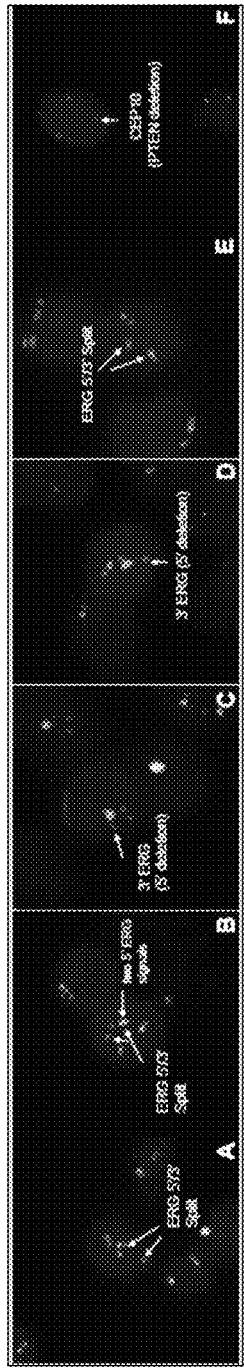
FIGS. 3A-3D show ERG and PTEN alterations in CK− and small CTCs, nuclear size distribution of CTCs and incidence of CK−CTC populations.

ERG and PTEN alterations in CK− and small CTCs were identified. As shown in FIG. 3A, FISH analysis was performed on patient samples where small and CK− cells were identified by IF. ERG and PTEN alterations in CK− and small CTCs were identified as follows: ERG insertion in small CTC (FIG. 3A, panel A); 5' ERG deletion in small CTC (FIG. 3A, panels B and C); 5' ERG deletion in CK− CTC (FIG. 3A, panel D); ERG insertion in CK− CTC (FIG. 3A, panel E); PTEN deletion in CK− CTC (FIG. 3A, panel F). CK− and small CTCs harboring ERG gene rearrangements and/or PTEN loss were identified (see FIG. 3A).

Figure 3B:
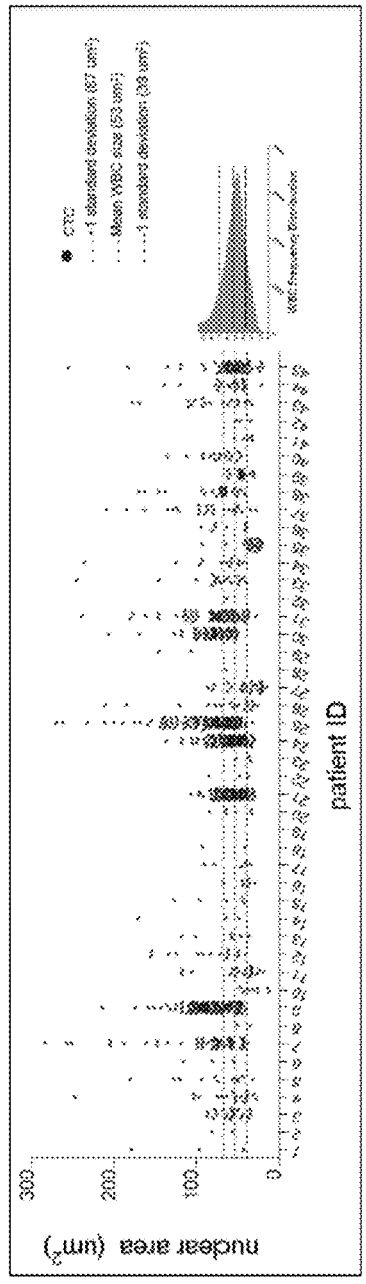

Nuclear size distribution of CTCs was also determined. CTCs with nuclear size similar to or smaller than WBCs can be identified and characterized on the Epic Sciences platform. These cells may or may not be detected with alternative methods that utilize size or density selection (see FIGS. 3B and 3C). FIG. 3B shows nuclear size per CTC as calculated by Epic software for each patient. 1.9 million normal WBCs were used to calculate the WBC mean and standard deviation. Green (upper) and black (lower) dashed lines indicate WBC size cutoffs equal to one standard deviation from the mean (+1 standard deviation, 67 µm$^2$, −1 standard deviation 39 µm$^2$, respectively; mean WBC size red (middle) dashed line, 53 µm$^2$). CTCs with nuclear size smaller than or within one standard deviation of the WBC mean are likely to be missed with size or density selection.

Figure 3C:
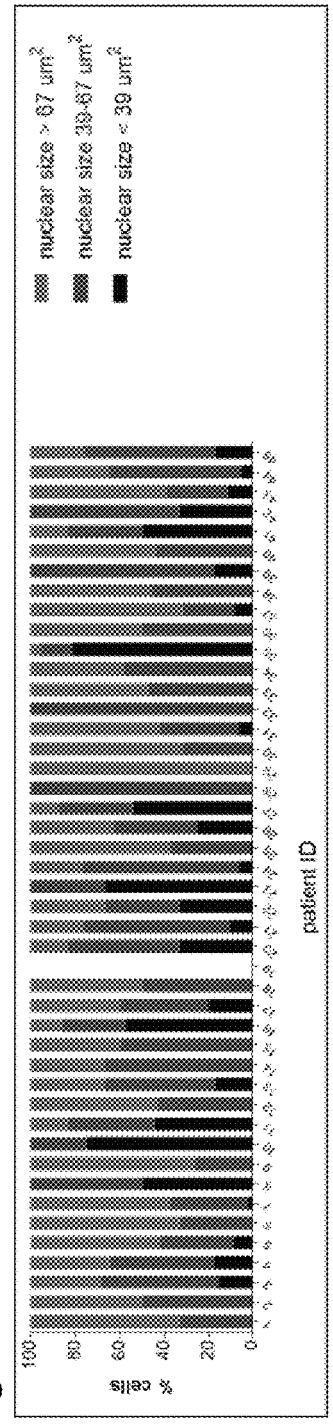

FIG. 3C shows percentage of cells with different nuclear sizes for each patient. The percentage of cells for each patient with nuclear size greater than one standard deviation from the WBC mean (green, upper in bar graph; nuclear size>67 µm$^2$), within one standard deviation of the mean (red, middle in bar graph; nuclear size=39-67 µm$^2$) and less than one standard deviation from the mean (black, lower in bar graph; nuclear size<39 µm$^2$). Cells represented in black and red are likely to be missed with size or density selection.

Figure 3D:
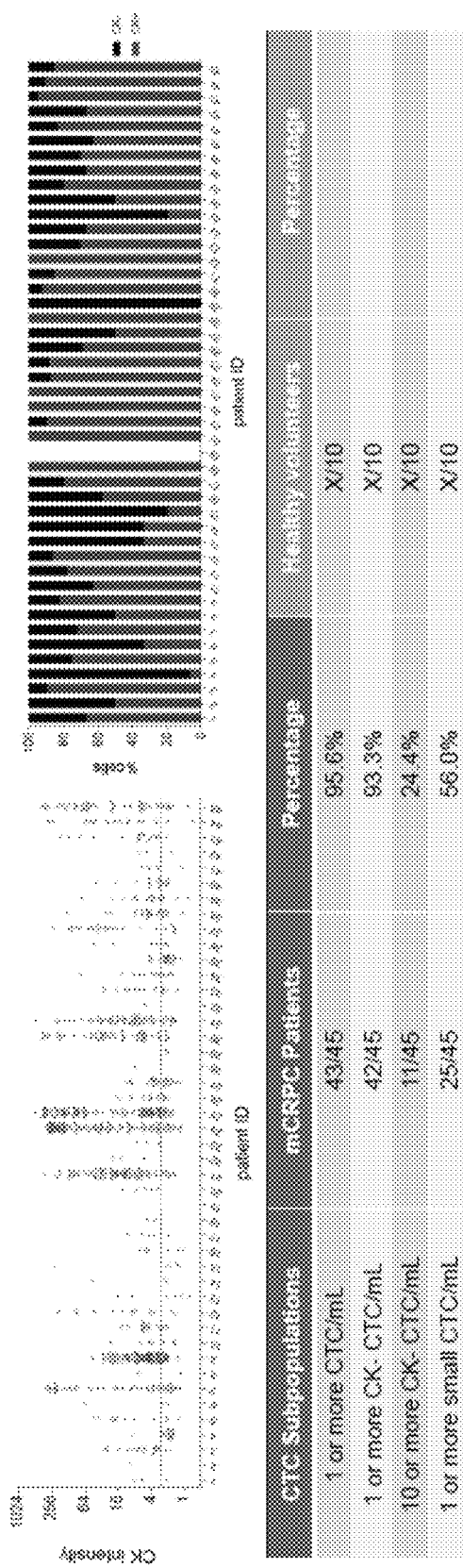

The incidence of CK− CTC subpopulations was determined. FIG. 3D, upper left panel, shows CK intensity per CTC per patient. Dashed line at 2.8 indicates cutoff for CK positivity. Cells with CK below 2.8 are detected based on abnormal morphology and AR positivity. FIG. 3D, upper right panel, shows the percentage of cells for each patient with CK+ (red, lower in bar graph) or CK− (black, upper in bar graph)) CTCs. Additional information on the CTC subpopulations is shown in FIG. 3D, lower panel.

Evidence suggests that CK−, CD45− circulating cells and small nuclear size CK+, CD45− cells are PCa derived CTCs. The frequency of small CTCs are associated with visceral metastasis and the presence of CK− CTCs may be associated with epithelial plasticity and may be a negative prognostic factor to patient overall survival. Finally, CTC isolation techniques utilizing size, density, EpCAM or CK positivity are likely to miss these potentially important CTCs through missampling of patient blood.

Example 3. Morphologic, Phenotypic and Genetic Characterization of CTC Diversity in Patients with mCRPC This example demonstrates the existence of distinct non-traditional CTC populations in mCRPC patients. Concurrent AR expression and FISH (for PTEN deletion or ERG rearrangement) was used to confirm prostate cancer origin of both traditional and non-traditional CTCs Briefly, as described in detail in this example, CTC analysis was performed on 41 patients with metastatic castration resistant prostate cancer (mCRPC) and 20 healthy volunteers using the Epic CTC Platform, which utilizes high throughput imaging of all circulating nucleated cells after plating on glass slides, DAPI staining and CD45 and cytokeratin (CK) immunofluorescence (IF). PCa specific alterations (IF for androgen receptor [AR] expression and fluorescence in situ hybridization [FISH] for PTEN and ERG) were also evaluated in select patients to assess PCa origin of CTCs. Traditional (t)CTCs (CD45$^-$/CK$^+$/abnormal morphology) were identified in 39 of 41 (95%) mCRPC patients (median 5 CTCs/mL blood). tCTCs expressing AR were detected in 28 of 39 (72%) patients, while PTEN or ERG aberrations were identified in tCTCs from 4 of the 6 (67%) tested patients (FISH platform scoring accuracy of 97%). Using AR positivity, ERG rearrangement and/or PTEN deletion as confirmation, we were able to identify non-traditional CTCs in mCRPC patients, including CK$^-$ (defined by CD45$^-$/CK$^-$/abnormal morphology), small (defined by CD45$^-$/CK$^+$/similar nuclear size to WBCs) and apoptotic CTCs (CD45$^-$/nuclear fragmentation or condensation). Positive correlation between tCTC and CK− CTCs, small CTCs and apoptotic CTCs, respectively, were observed (Searman's correlation r=0.62, p<0.001; r=0.42, p=0.006; and r=0.69, p<0.001; respectively).

Sample Collection and Handling. Whole blood samples were obtained from 41 unique stage IV mCRPC patients at the Institute for Cancer Research (ICR, Sutton, England) and shipped to Epic Sciences (San Diego, Calif., USA) at ambient temperature. Additionally, 21 samples were obtained from 20 consenting healthy adults by either ICR or Epic Sciences, and processed in the same manner as patient samples. Samples were collected with informed consent. Patient and healthy volunteer demographics are summarized in FIG. 11. The median blood sample transit time for patient samples was 32 hours with a range of 28-78 hours. Additional draws were performed on select patients as needed for FISH analysis.

Blood sample preparation and storage. Upon sample receipt, red blood cells were lysed and nucleated cells dispensed onto glass microscope slides according to methods previously described (Hsieh et al., Biosens. Bioelectron. 21:1893-1899 (2006); Marrinucci et al., Phys. Biol. 9:016003 (2012); Marrinucci et al., Hum. Pathol. 38: 514-519 (2007)) and stored at −80° C. for long term storage. Up to 12 slides were prepared from each blood sample at $3 \times 10^6$ cells/slide. The number of slides created from each individual sample was determined by the volume of blood received and the white blood cell (WBC) count. In our experience, CTC slides stored at −80 C using this approach are stable over 1 year (unpublished data).

CTC identification and protein characterization. CTC analysis was performed in batches of patient samples. Two slides from each patient sample were thawed, then stained by IF to distinguish CTCs from WBCs as described previously (Hsieh et al., Biosens. Bioelectron. 21:1893-1899 (2006); Marrinucci et al., Phys. Biol. 9:016003 (2012); Marrinucci et al., Hum. Pathol. 38: 514-519 (2007)). In addition to DAPI, CD45, and CK, an additional antibody targeting AR (Cell Signaling Technology, Danvers, Mass., USA) was utilized. Stained slides were imaged on a high-speed fluorescent imaging system. Captured images were analyzed by an automated algorithm that characterizes each cell by over 90 parameters, including protein expression and morphology to identify CTCs. All CTC candidates were then reviewed by trained technicians, and $CK^+/CD45^-$ cells with intact, $DAPI^+$ nuclei exhibiting tumor-associated morphologies were classified as traditional CTCs. Candidate non-traditional CTCs, as described below, were identified as $CD45^-/CK^-$ cells with abnormal morphology, $CD45^-/CK^+$ cells with small nuclear size (similar to or smaller than surrounding WBCs), and apoptotic CTCs ($CD45^-$ with characteristic nuclear fragmentation or condensation). In a separate subsequent analysis, cell morphological characteristics were determined for each CTC by Epic proprietary software. AR expression (IF) and PTEN loss (FISH), or ERG rearrangements (FISH) were compared in both traditional and non-traditional CTCs. Analysis was reviewed by a Board certified Anatomic Pathologist with experience in genitourinary pathology and molecular characterization of mCRPC (S.A.T.) to confirm cancer origin.

CTC FISH analysis. Following CTC identification and classification, a subset of slides with sufficient candidate CTCs were further tested for PTEN loss or ERG rearrangement by FISH. For PTEN FISH, coverslips were removed from slides, mounting medium was rinsed, and cells were fixed and dehydrated with formaldehyde and ethanol, respectively. After complete dehydration, a 2-color probe solution (Cymogen Dx, New Windsor, N.Y., USA) targeting PTEN DNA sequences and chromosome 10 centromeres (CEP10) was applied to each slide, and then hybridized for 18-24 hours at 37° C. Slides were then washed in saline sodium citrate (SSC)/Igepal solutions, counterstained with DAPI, and mounted with an anti-fade mounting medium. Epic software was used to relocate CTCs for scoring. 20 WBCs on each slide were also scored as internal controls. A subset of patients were tested for ERG rearrangements with FISH probes (Cymogen Dx, New Windsor, N.Y., USA) flanking (5' and 3') ERG following the same methods outlined above.

PTEN loss was defined by a cell containing fewer PTEN signals than CEP10 signals or only 1 of each signal (loss of chromosome 10). Cells with 0 PTEN signals and at least 1 CEP10 signal were classified as homozygous PTEN loss (HO). Heterozygous PTEN loss (HE) cells contained at least 1 PTEN signal and at least 1 more CEP10 signal than PTEN. Cells with 1 PTEN signal and 1 CEP10 signal were also considered to exhibit heterozygous PTEN loss. Cells with a 1:1 ratio of PTEN:CEP10 and at least 2 of each signal were considered PTEN-normal. ERG rearrangements can occur through two different mechanisms: rearrangement through insertion (resulting in a split 5' of 3' FISH signals) or deletion (resulting in loss of the 5' FISH signal). Hence, cells were considered ERG-rearranged if a separation of at least 1 pair of 5' and 3' ERG signals (by a distance of at least 2 signal diameters) or deletion of at least 1 5' ERG signal was observed. Cells in which all 3' ERG signals had a corresponding 5' ERG signal within 2 signal diameters were considered ERG-normal. The overall CTC-based PTEN or ERG status of each patient was determined by evaluating at least 7 CTCs.

Statistical Analysis. Correlations of traditional and non-traditional CTC counts were assessed by Spearman rank correlation test. P values<0.05 were considered significant.

Detection of Traditional CTCs in mCRPC patients. 21 blood samples from 20 healthy volunteers and 41 blood samples from 41 mCRPC patients were analyzed for the presence of CTCs using the Epic CTC Platform. Patient and healthy volunteer demographics are shown in FIG. 11. After red cell lysis, all nucleated cells from each blood sample were plated on glass slides and subjected to IF staining for DAPI, CD45, CK and AR followed by high speed imaging of the entire slide. For each patient, an average of 11 slides were plated (range 4 to 16), with an average blood volume of 7.0 mL (range 3.68-7.83 mL) plated per patient. Traditional CTCs were defined (described previously (Hsieh et al., Biosens. Bioelectron. 21:1893-1899 (2006); Marrinucci et al., Phys. Biol. 9:016003 (2012); Marrinucci et al., Hum. Pathol. 38: 514-519 (2007)) as cells with an intact, DAPI-positive nucleus lacking features of apoptosis, absence of CD45 staining ($CD45^-$) and positive CK staining ($CK^+$) (FIG. 10A). Additionally, traditional CTCs were required to have characteristic cytomorphologic features consistent with malignancy (including nucleomegaly, nuclear membrane irregularity, eccentric cytoplasmic distribution, and polygonal/elongated cell shapes) (Hsieh et al., Biosens. Bioelectron. 21:1893-1899 (2006); Marrinucci et al., Phys. Biol. 9:016003 (2012); Marrinucci et al., Hum. Pathol. 38: 514-519 (2007); Marrinucci et al., Arch. Pathol. Lab. Med. 133: 1468-1471 (2009)). Using this traditional CTC definition, 39/41 (95%) mCRPC patients had detectable traditional CTCs (median 5/mL, range 0-98) shown in FIG. 8. 5/20 (25%) healthy volunteers had detectable traditional CTCs (median 0/mL, range 0-4/mL). FIG. 9A shows the frequency of traditional CTCs in patient samples compared to healthy volunteer samples. When two or more adjacent traditional CTCs were identified, they were classified as CTC clusters. CTC clusters were detected in 7/41 (17%) patients (median 0/mL, range 0-6). CTC clusters were not detected in healthy volunteer samples.

Phenotypic/Molecular Characterization of Traditional CTCs. AR over-expression, loss of the PTEN tumor suppressor gene, and the TMPRSS2/ERG gene fusion are common molecular events in mCRPC and are useful to confirm prostatic origin of CTCs (Attard et al., Cancer Res. 69: 2912-2918 (2009); Beltran and Rubin, Clin. Cancer Res. 19: 517-523 (2013); Brenner et al., in Prostate Cancer: Biochemistry, Molecular Biology and Genetics, Tindall, ed., pp. 139-183, Springer New York. (2013); Grasso et al., Nature 487: 239-243 (2012)). For example, ERG gene rearrangements are nearly 100% specific for prostate cancer compared to benign prostate epithelium, and ERG rearrangements have not been reported in any other epithelial cancers (Brenner et al., in Prostate Cancer: Biochemistry, Molecular Biology and Genetics, Tindall, ed., pp. 139-183, Springer New York. (2013)).

AR expression was evaluated in all mCRPC patients and select healthy volunteers. To generate a relative AR expression value for each CTC, Epic's software normalized AR expression in CTCs to approximately 1 million surrounding $CD45^+$ WBCs present on the same slide. CTCs with AR expression values>3.0 were considered positive. Across the 39 mCRPC patients with detectable traditional CTCs, 28 (72%) had at least one AR positive traditional CTC/mL (range 0-84) and a median of 34% (range 0%-100%) of the traditional CTCs showed AR expression (mean intensity 7.2, range 0.9-143.2) by IF. The proportion of $AR^+$ vs. $AR^-$ traditional CTCs varied across patients within the cohort (FIG. 10A). Previous studies have demonstrated loss of AR expression (and/or downstream targets) in CTCs or tissues from advanced CRPC, consistent with androgen independence (Miyamoto et al., Cancer Discov. 2: 995-1003 (2012); Shah et al., Cancer Res 64: 9209-9216 (2004); Roudier et al., Hum. Pathol. 34: 646-653 (2003)). As a comparison, select healthy volunteer samples from 5 patients (n=6) with detectable CTCs were tested for AR expression. 2/6 (33%) samples had at least one AR' traditional CTC/mL (range 0-1) and a median of 0% (range 0%-50%) of the traditional CTCs showed AR expression (mean intensity 5.3, range 3.7-6.85).

To further establish the prostatic origin of CTCs in our cohort, we assessed their PTEN/ERG status by FISH, using surrounding WBCs as internal controls. Among slides from healthy volunteers, none had sufficient detectable CTCs to perform PTEN/ERG assessment. Hence, to first determine assay specificity, we assessed PTEN/ERG status of WBCs from the patient slides that were tested by PTEN/ERG FISH. Of 120 patient WBCs evaluated with PTEN FISH, 3 (2.5%) and 0 (0.0%) cells were detected with PTEN heterozygous (HE) and homozygous (HO) loss, respectively, resulting in 97.5-100% specificity of the PTEN FISH test on the Epic platform. Of 60 patient WBCs evaluated with ERG FISH, 2 (3.3%) and 0 (0.0%) cells with ERG(insertion) and ERG (deletion), respectively, resulting in 96.7-100% specificity of the ERG FISH test on the Epic platform.

After IF staining for AR and CTC detection on the Epic platform, CTCs from 5 mCRPC patients were then relocated and evaluated by PTEN FISH. PTEN deletions were detected in traditional CTCs in 4 of 5 patients tested (FIG. 12A). Likewise, 2 of 3 patients with traditional CTCs evaluated by ERG FISH had ERG rearrangement (FIG. 12B). FIG. 10B shows representative images of traditional CTC's with AR expression and/or PTEN deletion/ERG rearrangement. Together, these results demonstrate the utility of this assay to characterize CTC populations with tumor type specific markers, verifying the prostatic origin of traditional CTCs in this cohort.

Detection of Non-traditional CTCs in mCRPC patients. A potential advantage of the Epic CTC Platform is the non-biased analysis of all cells within a sample, including potential CTCs with atypical characteristics that may be excluded with EpCAM/CK or sized based enrichment modalities. We evaluated AR expression (in all cases), and PTEN deletion and ERG rearrangement in a subset of patients to support prostate cancer origin for circulating cells that did not meet the strict definition of traditional CTCs. As described in detail below, we identified three categories of cells with non-traditional phenotypes that were potential CTCs: cells the same size or smaller than neighboring leukocytes (small CTCs), cells with dim or no cytokeratin expression ($CK^-$ CTCs), and cells with degenerative changes and nuclear disintegration consistent with apoptosis (apoptotic CTCs). As shown in FIG. 8, all patients with traditional CTCs also harbored circulating cells with these non-traditional phenotypes (a median of 7/mL per patient, range 2-104). Four of the 20 (20%) healthy volunteers also had circulating cells that met these expanded CTC criteria (median 0/mL per patient, range 0-5) and each had at least 1 cell with AR positivity (median 1/mL per patient, range 0-4) with mean AR intensity of 5.8 (range 1.1-34.4). FIG. 9B shows the frequency of non-traditional CTCs in patient samples compared to healthy volunteer samples.

Small CTCs in mCRPC patients. As per traditional analysis of CTCs, small CTCs are identified by trained scorers who classify $CD45^-/CK^+$ cells based upon a visual estimation of the nuclear size relative to the WBCs directly adjacent to the CTC. As defined, small CTCs were detected in 19/41 (46%) mCRPC patients, with a median of 0 small CTCs/mL per patient (range 0-23) as shown in FIG. 8. A positive correlation between counts of traditional CTCs and small CTCs in patients with mCRPC ($r_s$=0.42, p=0.006; Spearman's correlation) was observed. When assessed for AR expression, small CTCs exhibited heterogeneous AR expression, with a median percentage of AR expressing small CTCs of 0% per patient (range 0-67%), with a mean AR intensity of 3.5 (range 1.0-35.6). Additionally, small CTCs were evaluated by FISH for ERG and PTEN aberrations. We were able to evaluate 11 small CTCs from 1 patient for ERG FISH and found rearrangements in 3 out of 11 (27.3%) (FIG. 12). ERG rearrangements were also detected in 3/39 (7.7%) traditional CTCs in this patient. The size of small CTCs precluded interpretation of PTEN deletions in all but 1 CTC, which was wild type. Examples of small CTCs harboring AR positivity or ERG alterations by FISH are shown in FIG. 10B.

Given that visual estimation of nuclear size may vary based upon scorer interpretation, regional pre-analytics, and staining, we also utilized Epic software to objectively measure the total area of each cell and to more robustly identify small CTC subpopulations (FIG. 8A) within mCRPC patient samples. Approximately 300 patient WBCs were used to generate the median and interquartile ranges for WBC area (75 $\mu m^2$ and 64-90 $\mu m^2$, respectively) with a cell area≤90 $\mu m^2$ used to define small CTCs. By this approach, cell area of traditional and non-traditional CTC subtypes was evaluated, however apoptotic CTCs were omitted because of poor segmentation due to the fragmented cell morphology of dead or dying cells. We observed a wide range of CTC sizes within individual patients and across the mCRPC patient cohort using this objective assessment, with small CTCs detectable in 41/41 (100%) mCRPC patients (FIG. 8B).

Cytokeratin negative CTCs in mCRPC patients. Cytokeratin intensity in $CD45^-$ circulating cells with abnormal morphology varied widely across patients with mCRPC (FIG. 9A). As with AR expression measurements, relative cytokeratin expression values for each CTC were generated by Epic's software, normalizing CK expression in CTCs to approximately 1 million surrounding $CD45^+$ WBCs present on the same slide. CTCs with CK expression values>2.8 were considered positive. Hence, we defined non-traditional $CK^-$ CTCs as $CD45^-$ circulating cells with morphological distinction and/or AR positivity, but CK intensity less than 2.8. Such $CK^-$ CTCs were identified in 35/41 (85%) mCRPC patients, with a median of 3 $CK^-$ CTCs/mL per patient (range 0-17) as shown in FIG. 8. Amongst CK⁻ CTCs, a median of 75% (range 0-100%) per patient showed AR expression (mean intensity 4.1, range 0.9-25.3). The proportion of CK⁺/CK⁻ CTCs varied across the cohort, with 4 patients demonstrating a CTC population that was predominantly CK– (FIG. 9B). Traditional CTC and CK⁻ CTC counts in mCRPC patients were positively correlated ($r_s$=0.62, p<0.001). PTEN or ERG FISH was performed on select patients with CK⁻ CTCs. PTEN deletions were identified in 5/18 (28%) CK⁻ CTCs and ERG alterations were detected in 1/15 (7%) CK– CTCs (FIG. 12). Representative images of these cells are shown in FIG. 10B.

Apoptotic CTCs in mCRPC patients. CD45⁻/CK⁺ cells with nuclear fragmentation or condensation characteristic of apoptosis were also observed across the mCRPC cohort. These cells, which we classified as non-traditional apoptotic CTCs, were detected in 98% (40 of 41) of mCRPC patients (median 4/mL, range 0-92) as shown in FIG. 8. A median of 40% of the apoptotic CTCs (range 0-100%) expressed AR (mean intensity 4.4, range 0.9-92.8). Similar to the other categories of non-traditional CTCs, the frequency of apoptotic CTCs varied within mCRPC patients, with 9 patients exhibiting CTC populations composed primarily of apoptotic CTCs (FIG. 10). Traditional and non-traditional apoptotic CTC counts in mCRPC patients were positively correlated ($r_s$=0.69, p<0.001).

This example demonstrates the existence of multiple classes of non-traditional CTCs in patients with mCRPC. In addition to characterization by DAPI, CD45 and CK to define traditional CTCs (DAPI+/CD45–/CK+/abnormal morphology), this platform allows the non-biased identification of additional CTC cells not traditionally included by approaches using capture or size based exclusion criteria. Furthermore, this approach enables molecular characterization of candidate CTCs, both prior to and following slide scanning with single cell resolution. This example further demonstrates detection of prostate cancer associated molecular events, such as AR overexpression by IF and PTEN/ERG alterations by FISH in both traditional and non-traditional CTCs. Importantly, the presence and heterogeneity of AR expression, PTEN deletions and/or ERG rearrangements in both traditional and non-traditional CTCs confirms prostatic cancer origin and a heterogeneous model of advanced disease.

The results demonstrate that patients with mCRPC often harbor substantial subpopulations of traditional and non-traditional CTCs including those without cytokeratin expression (CK– CTCs), those with nuclear size similar to or smaller than WBCs (small CTCs), and those with nuclear or cellular features consistent with apoptosis (apoptotic CTCs). Although non-traditional CTC counts correlated with traditional CTC counts across the cohort of patients with mCRPC, substantial variation in the proportions of traditional to non-traditional CTCs was observed. Importantly, many of the non-traditional CTCs we identified would likely be missed by CTC detection platforms using antigen capture (i.e. EpCAM or CK) or size selection/filtration.

The detection of significant populations of non-traditional CTCs in mCRPC patients is consistent with substantial evidence supporting their existence and clinical relevance (based on atypical antigen expression or cellular size). For example, CTCs postulated to have undergone epithelial to mesenchymal transition (EMT), and display reduced or no EpCAM or cytokeratin expression, have been identified by multiple platforms using both cell line studies and patient blood samples (Ozkumur et al., Sci. Transl. Med. 5: 179ra147 (2013); Zhang et al., Sci. Transl. Med. 5: 180ra148 (2013); Yu et al., Science 339: 580-584 (2013); Pecot et al., Cancer Discov. 1: 580-586 (2011); Watanabe et al., Cytometry A 85:206-213 (2014); Giordano et al., Mol. Cancer Ther. 11: 2526-2534 (2012); Gorges et al., BMC Cancer 12: 178 (2012)). Populations of CTCs undergoing EMT have been postulated to harbor an increased subpopulation of multipotent cancer stem cells, with increased self-renewing and metastasis forming capacity Kalluri and Weinberg, J. Clin. Invest. 119: 1420-1428 (2009); Scheel and Weinberg, Semin. Cancer Biol. 22: 396-403 (2012)).

What is claimed is:

1. A method for detecting progression of prostate cancer to castration-resistant prostate cancer (CRPC) in a patient comprising (a) performing a direct analysis comprising immunofluorescent staining and morphological characterization of nucleated cells in a blood sample obtained from the patient to detect morphological and protein biomarkers of circulating tumor cells (CTC), wherein the CTCs are present among the nucleated cells subjected to the direct analysis at a frequency of less than 1 in 1,000 nucleated cells; (b) determining prevalence of a CTC subpopulation associated with CRPC comprising detecting a measurable feature of each of the biomarkers, wherein determining prevalence of the CTC subpopulation associated with CRPC comprises determining the prevalence of CTCs that have a nuclear size less than 67 $\mu m^2$, and wherein the presence of the CTC subpopulation associated with CRPC is indicative of CRPC, (c) repeating steps (a) and (b), wherein an increase in the prevalence of the presence of the CTC population associated with CRPC indicates progression of prostate cancer to CRPC; and (d) treating the patient with either (i) androgen deprivation therapy (ADT) if the prevalence has not increased, or (ii) a cancer therapy other than ADT if the prevalence has increased.

2. The method of claim 1, wherein the CRPC is metastatic castration-resistant prostate cancer (mCRPC).

3. The method of claim 2, wherein said patient is undergoing androgen deprivation therapy (ADT).

4. The method of claim 1, wherein the cancer therapy other than ADT comprises secondary hormonal therapy directed at AR inhibition.

5. The method of claim 4, wherein the secondary hormonal therapy directed at AR inhibition comprises treatment with abiraterone, enzalutamide, ketoconazole, or an estrogen.

6. The method of claim 1, wherein the ADT is a lueteinizing hormone-releasing hormone (LHRH) receptor agonist.

7. The method of claim 6, wherein the LHRH receptor agonist is leuprolide or goserelin.

8. The method of claim 1, wherein the cancer therapy other than ADT comprises treatment with chemotherapy, immunotherapy, or a radiopharmaceutical.

9. The method of claim 8, wherein the cancer therapy other than ADT comprises treatment with chemotherapy selected from docetaxel, mitoxantrone, paclitaxel, and cabazitaxel.

10. The method of claim 1, wherein said increase in the prevalence of the CTC population associated with CRPC predicts resistance to androgen deprivation therapy (ADT).

11. The method of claim 1, wherein the nucleated cells subjected to direct analysis are not enriched for a subpopulation of the nucleated cells as a proportion of the nucleated cells relative to the blood sample originally obtained from the patient.

12. The method of claim 1, wherein the nucleated cells subjected to direct analysis are not enriched for CTCs as a proportion of the nucleated cells relative to the blood sample originally obtained from the patient.

13. The method of claim 1, wherein the immunofluorescent staining comprises staining for the presence of cytokeratin, CD45, and androgen receptor.

14. The method of claim 1, wherein the CTCs are present among the nucleated cells subjected to the direct analysis at a frequency of less than 1 in 10,000 nucleated cells.

* * * * *